US012797231B2

(12) United States Patent
Carlsson et al.

(10) Patent No.: US 12,797,231 B2
(45) **Date of Patent: *Nov. 17, 2026**

(54) LEAKAGE DETECTION SYSTEM FOR OSTOMY APPLIANCE

(71) Applicant: HOLLISTER INCORPORATED, Libertyville, IL (US)

(72) Inventors: Jonas P. Carlsson, Chicago, IL (US); Ryan S. Park, Northbrook, IL (US); Stephanie Musinsky, Raleigh, NC (US); Scott E. Liddle, Raleigh, NC (US); Kyle A. Matthews, Chapel Hill, NC (US); Michael P. Nolan, Chicago, IL (US); Lauren M. Lattanzi, Raleigh, NC (US); Anthony B. Smith, Durham, NC (US); Christina Augustyn, Chicago, IL (US)

(73) Assignee: HOLLISTER INCORPORATED, Libertyville, IL (US)

( * ) Notice: Subject to any disclaimer, the term of this patent is extended or adjusted under 35 U.S.C. 154(b) by 243 days.

This patent is subject to a terminal disclaimer.

(21) Appl. No.: 18/884,325

(22) Filed: Sep. 13, 2024

(65) Prior Publication Data

US 2025/0000682 A1 Jan. 2, 2025

Related U.S. Application Data

(63) Continuation of application No. 17/616,950, filed as application No. PCT/US2020/037744 on Jun. 15, 2020, now Pat. No. 12,161,578.

(Continued)

(51) Int. Cl.

| | |
|---|---|
| *A61F 5/443* | (2006.01) |
| *A61F 5/44* | (2006.01) |
| *G01M 3/16* | (2006.01) |

(52) U.S. Cl.
CPC ............ *A61F 5/4404* (2013.01); *A61F 5/443* (2013.01); *G01M 3/16* (2013.01)

(58) Field of Classification Search
CPC .......... A61F 5/4404; A61F 5/443; G01M 3/16
See application file for complete search history.

(56) References Cited

U.S. PATENT DOCUMENTS 2,327,514 A * 8/1943 Fenwick ................. A61F 5/445 604/338
2,542,233 A * 2/1951 Carroll .................... A61F 5/445 604/337

(Continued)

FOREIGN PATENT DOCUMENTS

CN 101394817 A 3/2009
CN 102470041 A 5/2012

(Continued)

OTHER PUBLICATIONS

European Search Report issued in connection with EP application No. 25160385.8 dated May 16, 2025, 06 pages.

(Continued)

*Primary Examiner* — Guy K Townsend
(74) *Attorney, Agent, or Firm* — Klintworth & Rozenblat LLP

(57) ABSTRACT

An ostomy device includes a proximal side configured for attachment to a user, a distal side opposite to the proximal side, and a leakage detection sensor having electrically conductive circuitry supported on a support layer. The leakage detection sensor is configured to detect ostomy effluent by detecting a change in resistance in the electrically conductive circuitry. The ostomy device may be an ostomy appliance or an ostomy accessory.

21 Claims, 11 Drawing Sheets

Related U.S. Application Data

(60) Provisional application No. 63/029,053, filed on May 22, 2020, provisional application No. 63/028,008, filed on May 21, 2020, provisional application No. 62/861,508, filed on Jun. 14, 2019.

(56) References Cited

U.S. PATENT DOCUMENTS 2,544,579 A * 3/1951 Ardner .................... A61F 5/445 604/337
5,672,163 A * 9/1997 Ferreira .................. A61F 5/441 604/333
6,135,986 A * 10/2000 Leisner ................... A61F 5/441 604/324
6,171,289 B1 * 1/2001 Millot ..................... A61F 5/443 604/336
7,166,091 B1 * 1/2007 Zeltner ................... A61F 5/445 604/338
7,326,190 B2 * 2/2008 Botten .................... A61F 5/441 604/332
7,341,578 B2 * 3/2008 Bulow .................... A61F 5/441 604/338
7,367,965 B2 * 5/2008 Poulsen .................. A61F 5/441 604/324
7,559,922 B2 * 7/2009 Botten .................... A61F 5/441 604/332
7,625,362 B2 * 12/2009 Boehringer ............. A61M 1/74 604/304
7,981,098 B2 * 7/2011 Boehringer ............. A61M 1/74 604/319
8,398,603 B2 * 3/2013 Thirstrup ............... A61B 5/746 602/41
8,409,158 B2 * 4/2013 Edvardsen .............. A61F 5/443 604/335
8,684,982 B2 * 4/2014 Nguyen-DeMary .... A61F 5/441 604/327
9,066,812 B2 * 6/2015 Edvardsen .............. A61F 5/443
9,216,104 B2 * 12/2015 Thirstrup ............... A61B 5/746
9,308,332 B2 * 4/2016 Heppe ..................... A61M 1/30
10,016,298 B2 * 7/2018 Thirstrup ............... A61B 5/746
10,500,084 B2 * 12/2019 Hansen ................. A61F 5/4404
10,646,370 B2 * 5/2020 Keleny ............... A61F 13/0008
10,799,385 B2 * 10/2020 Hansen ................... G01M 3/40
10,849,781 B2 * 12/2020 Hansen ................ G01N 27/041
10,987,243 B2 * 4/2021 Thirstrup ............... A61B 5/746
11,096,818 B2 * 8/2021 Thirstrup ............... A61B 5/746
11,491,042 B2 * 11/2022 Seres ...................... A61F 5/443
11,534,323 B2 * 12/2022 Hansen .................. G16H 30/40
11,547,595 B2 * 1/2023 Hansen ................ A61B 5/6833
11,547,596 B2 * 1/2023 Hansen ..................... A61F 5/44
11,559,423 B2 * 1/2023 Speiermann ............ A61F 5/445
11,559,426 B2 * 1/2023 Sletten .................... A61F 5/443
12,161,578 B2 * 12/2024 Carlsson ................. G01M 3/16
2005/0070863 A1 * 3/2005 Bulow .................... A61F 5/441 604/338
2005/0085779 A1 * 4/2005 Poulsen .................. A61F 5/441 604/332
2005/0261645 A1 * 11/2005 Conrad ................... A61F 5/445 604/332
2006/0025727 A1 * 2/2006 Boehringer ........... A61M 1/966 604/313
2006/0271002 A1 * 11/2006 Botten .................... A61F 5/441 604/339
2008/0087361 A1 4/2008 Stommel
2008/0091154 A1 * 4/2008 Botten .................... A61F 5/441 96/155
2008/0097361 A1 4/2008 Fabo et al.
2008/0275327 A1 * 11/2008 Faarbaek ............. A61B 5/0002 600/382
2009/0012501 A1 * 1/2009 Boehringer ........... A61M 1/966 604/543
2009/0247970 A1 * 10/2009 Keleny .............. B01D 46/0036 156/247
2010/0010460 A1 * 1/2010 Butler ..................... A61F 5/441 604/333
2010/0030167 A1 * 2/2010 Thirstrup ............... A61B 5/746 340/657
2012/0143154 A1 * 6/2012 Edvardsen ............ A61F 5/4404 604/336
2012/0143155 A1 * 6/2012 Edvardsen .............. A61F 5/443 604/318
2012/0283678 A1 * 11/2012 Nguyen-DeMary .... A61F 5/445 604/338
2012/0302981 A1 11/2012 Lam
2013/0072886 A1 * 3/2013 Schertiger ............... A61F 5/441 604/335
2013/0150769 A1 * 6/2013 Heppe ..................... A61M 1/30 604/6.16
2013/0192604 A1 * 8/2013 Persson ............... A61M 16/047 128/207.16
2013/0231620 A1 * 9/2013 Thirstrup ............... A61B 5/746 604/344
2014/0163496 A1 6/2014 Grum-Schwensen et al.
2014/0276501 A1 * 9/2014 Cisko ...................... A61F 5/443 604/355
2014/0288381 A1 * 9/2014 Faarbaek ............. A61B 5/0002 600/300
2015/0250639 A1 * 9/2015 Thirstrup ............... A61B 5/746 156/278
2016/0158056 A1 * 6/2016 Davis ...................... A61F 5/443 29/872
2016/0166438 A1 * 6/2016 Rovaniemi .............. A61B 5/00 493/320
2016/0235581 A1 * 8/2016 Keleny ............... A61F 13/0008
2017/0140103 A1 * 5/2017 Angelides ............. A61F 5/4404
2017/0340474 A1 * 11/2017 Thirstrup ............... A61B 5/746
2018/0344533 A1 * 12/2018 Rovaniemi ....... A61F 13/00063
2019/0133810 A1 * 5/2019 Seres ...................... A61F 5/443
2019/0133811 A1 * 5/2019 Seres ...................... A61F 5/443
2019/0133812 A1 * 5/2019 Seres ...................... A61F 5/443
2019/0142623 A1 5/2019 Schoess et al.
2019/0175386 A1 * 6/2019 Monty ................ A61F 13/0266
2019/0192332 A1 * 6/2019 Hansen ................ A61B 5/7475
2019/0192333 A1 * 6/2019 Hansen ................ G01N 27/041
2019/0192334 A1 * 6/2019 Hansen ................... A61F 5/445
2019/0240059 A1 8/2019 Seres et al.
2019/0247050 A1 * 8/2019 Goldsmith ................ A61F 2/82
2019/0374163 A1 * 12/2019 Faarbaek ............. A61B 5/0002
2019/0374372 A1 * 12/2019 Seres ...................... A61F 5/443
2020/0000624 A1 1/2020 Gibbons et al.
2020/0188161 A1 * 6/2020 Seres ...................... A61F 5/445
2020/0246174 A1 * 8/2020 Hansen ................... A61F 5/443
2020/0246175 A1 * 8/2020 Hansen ................ A61B 5/0002
2020/0246176 A1 * 8/2020 Hansen ................... A61F 5/445
2020/0246177 A1 * 8/2020 Hansen ................ A61B 5/4255
2020/0306074 A1 * 10/2020 Speiermann .......... A61F 5/4404
2020/0330258 A1 * 10/2020 Hansen ................... A61F 5/443
2020/0330260 A1 * 10/2020 Hansen .................. G16H 50/30
2020/0337880 A1 * 10/2020 Hansen ..................... A61F 5/44
2020/0337881 A1 * 10/2020 Hansen ................ A61B 5/4851
2020/0337883 A1 * 10/2020 Hansen ................ A61F 5/4404
2020/0375784 A1 * 12/2020 Hansen ................ A61F 5/4404
2020/0375785 A1 * 12/2020 Hansen ................ A61B 90/361
2020/0375786 A1 * 12/2020 Hansen ................ A61F 5/4404
2020/0383637 A1 * 12/2020 Hansen ................ A61F 5/4404
2020/0383818 A1 * 12/2020 Hansen ................... A61F 5/443
2020/0383819 A1 * 12/2020 Sletten .................... A61F 5/443
2020/0383820 A1 * 12/2020 Hansen ................ A61B 5/0004
2020/0383821 A1 * 12/2020 Hansen ..................... A61F 5/44
2020/0390587 A1 * 12/2020 Svanegaard .......... A61F 5/4404
2020/0390588 A1 * 12/2020 Hansen ................ A61F 5/4404
2020/0390589 A1 * 12/2020 Hansen .................. A61B 5/683
2020/0395120 A1 * 12/2020 Svanegaard .......... A61F 5/4404
2020/0405228 A1 * 12/2020 Svanegaard ......... A61B 5/4851
2020/0405229 A1 * 12/2020 Svanegaard ......... A61B 5/4851
2020/0405230 A1 * 12/2020 Svanegaard ......... A61B 5/6813
2021/0000414 A1 * 1/2021 Svanegaard ......... A61B 5/4851
2021/0000633 A1 * 1/2021 Hansen ................ A61F 5/4404
2021/0000634 A1 * 1/2021 Svanegaard ......... A61B 5/0004
2021/0000635 A1 * 1/2021 Hansen ................... A61F 5/443
2021/0007663 A1 * 1/2021 Svanegaard ......... A61B 5/4851

(56) References Cited

U.S. PATENT DOCUMENTS

| | | | | |
|---|---|---|---|---|
| 2021/0007881 | A1* | 1/2021 | Svanegaard | A61F 5/4404 |
| 2021/0015654 | A1* | 1/2021 | Hansen | A61F 5/445 |
| 2021/0038424 | A1* | 2/2021 | Svanegaard | A61B 5/1112 |
| 2021/0059603 | A1* | 3/2021 | Svanegaard | A61B 5/4851 |
| 2021/0085511 | A1* | 3/2021 | Hansen | A61F 5/445 |
| 2021/0085512 | A1* | 3/2021 | Hansen | A61F 5/448 |
| 2021/0100533 | A1* | 4/2021 | Seres | A61B 5/0024 |
| 2021/0177642 | A1* | 6/2021 | Andersen | A61F 5/4404 |
| 2021/0212855 | A1* | 7/2021 | Hansen | A61F 5/4404 |
| 2021/0275341 | A1 | 9/2021 | Hansen | |
| 2021/0338471 | A1* | 11/2021 | Nolan | A61F 5/4404 |
| 2021/0353448 | A1 | 11/2021 | Fattman et al. | |
| 2021/0361464 | A1* | 11/2021 | Larsen | A61F 5/44 |
| 2021/0361465 | A1* | 11/2021 | Hansen | A61B 5/4851 |
| 2021/0361467 | A1* | 11/2021 | Hansen | A61B 5/1118 |
| 2021/0369197 | A1* | 12/2021 | Hansen | A61B 5/4851 |
| 2021/0369488 | A1* | 12/2021 | Hansen | A61B 5/0002 |
| 2021/0369489 | A1* | 12/2021 | Hansen | A61F 5/44 |
| 2021/0369490 | A1* | 12/2021 | Hansen | A61F 5/44 |
| 2021/0369491 | A1 | 12/2021 | Holden | |
| 2022/0117771 | A1 | 4/2022 | Fearn et al. | |
| 2022/0257405 | A1 | 8/2022 | Moeller et al. | |
| 2022/0265457 | A1 | 8/2022 | Emborg et al. | |
| 2022/0313473 | A1 | 10/2022 | Schertiger et al. | |
| 2022/0378602 | A1* | 12/2022 | Hansen | A61F 5/4404 |
| 2023/0031979 | A1 | 2/2023 | Windeballe et al. | |

FOREIGN PATENT DOCUMENTS

| | | | |
|---|---|---|---|
| CN | 102711680 | A | 10/2012 |
| DE | 19953062 | A1 | 5/2000 |
| FR | 7013 | E | 5/1907 |
| JP | H11178855 | A | 7/1999 |
| KR | 20180035536 | A | 4/2018 |
| WO | WO2000/079497 | A1 | 12/2000 |
| WO | WO2017/088153 | A1 | 6/2017 |
| WO | WO2019/094635 | A1 | 5/2019 |
| WO | WO2019/120424 | A1 | 6/2019 |
| WO | WO2019/120425 | A1 | 6/2019 |
| WO | WO2019/120426 | A1 | 6/2019 |
| WO | WO2019/120427 | A1 | 6/2019 |
| WO | WO2019/120428 | A1 | 6/2019 |
| WO | WO2019/120429 | A1 | 6/2019 |
| WO | WO2019/120430 | A1 | 6/2019 |
| WO | WO2019/120432 | A1 | 6/2019 |
| WO | WO2019/120433 | A1 | 6/2019 |
| WO | WO2019/120434 | A1 | 6/2019 |
| WO | WO2019/120435 | A1 | 6/2019 |
| WO | WO2019/120436 | A1 | 6/2019 |
| WO | WO2019/120437 | A1 | 6/2019 |
| WO | WO2019/120440 | A1 | 6/2019 |
| WO | WO2019/120441 | A1 | 6/2019 |
| WO | WO2019/120442 | A1 | 6/2019 |
| WO | WO2019/120443 | A1 | 6/2019 |
| WO | WO2019/120444 | A1 | 6/2019 |
| WO | WO2019/120445 | A1 | 6/2019 |
| WO | WO2019/120446 | A1 | 6/2019 |
| WO | WO2019/120448 | A1 | 6/2019 |
| WO | WO2019/120449 | A1 | 6/2019 |
| WO | WO2019/120450 | A1 | 6/2019 |
| WO | WO2019/120451 | A1 | 6/2019 |
| WO | WO2019/120452 | A1 | 6/2019 |
| WO | WO2019/120453 | A1 | 6/2019 |
| WO | WO2019/120458 | A1 | 6/2019 |
| WO | WO2019/149330 | A1 | 8/2019 |
| WO | WO2019/161859 | A1 | 8/2019 |
| WO | WO2019/161860 | A1 | 8/2019 |
| WO | WO2019/161861 | A1 | 8/2019 |
| WO | WO2019/161862 | A1 | 8/2019 |
| WO | WO2019/161863 | A1 | 8/2019 |
| WO | WO2019/174687 | A1 | 9/2019 |
| WO | WO2019/174692 | A1 | 9/2019 |
| WO | WO2019/174693 | A1 | 9/2019 |
| WO | WO2019/174694 | A1 | 9/2019 |
| WO | WO2019/174695 | A1 | 9/2019 |
| WO | WO2019/174696 | A1 | 9/2019 |
| WO | WO2019/174697 | A1 | 9/2019 |
| WO | WO2019/174698 | A1 | 9/2019 |
| WO | WO2019/174699 | A1 | 9/2019 |
| WO | WO2019/238180 | A1 | 12/2019 |
| WO | WO2019/238181 | A1 | 12/2019 |
| WO | WO2019/238182 | A1 | 12/2019 |
| WO | WO2019/238183 | A1 | 12/2019 |
| WO | WO2020/035121 | A1 | 2/2020 |
| WO | WO2020/123771 | A2 | 6/2020 |
| WO | WO2020/156624 | A1 | 8/2020 |
| WO | WO2020/156625 | A1 | 8/2020 |
| WO | WO2020/156626 | A1 | 8/2020 |
| WO | WO2020/169162 | A1 | 8/2020 |
| WO | WO2020/173534 | A1 | 9/2020 |
| WO | WO2020/216426 | A1 | 10/2020 |
| WO | WO2020/216427 | A1 | 10/2020 |
| WO | WO2020/216429 | A1 | 10/2020 |
| WO | WO2020/259775 | A1 | 12/2020 |
| WO | WO2021/063463 | A1 | 4/2021 |
| WO | WO2021/063466 | A1 | 4/2021 |
| WO | WO2021/165703 | A1 | 8/2021 |
| WO | WO2021/165705 | A1 | 8/2021 |
| WO | WO2021/185425 | A1 | 9/2021 |
| WO | WO2021/209104 | A1 | 10/2021 |
| WO | WO2022/063379 | A1 | 3/2022 |
| WO | WO2022/078561 | A1 | 4/2022 |
| WO | WO2022/207049 | A1 | 10/2022 |

OTHER PUBLICATIONS

Canadian Office Action issued in connection with CA application No. 3,143,202 dated Nov. 4, 2025, 09 pages.

Chinese office Action issued in connection with CN application No. 202080049744.6 dated Apr. 16, 2025, 12 pages.

International Search Report issued by ISA/EPO in connection with PCT/US2020/037744 on Oct. 9, 2020.

Written Opinion issued by ISA/EPO in connection with PCT/US2020/037744 on Dec. 14, 2021.

The State Intellectual Property Office of the People's Republic of China Official Action for Application No. 202080049744.6 , dated Apr. 27, 2024, 4 pages.

Chinese Search report issued in connection with CN application No. CN20208049744.6 dated Apr. 27, 2024, 02 pages.

* cited by examiner

114

LEAKAGE DETECTION SYSTEM FOR OSTOMY APPLIANCE

This is a Continuation of U.S. application Ser. No. 17/616,950 filed dated Dec. 6, 2021 which is a National Stage Application of International Patent Application No. PCT/US2020/037744 filed Jun. 15, 2020, which claims the benefit of and priority to U.S. Provisional Application No. 62/861,508 filed Jun. 14, 2019, U.S. Provisional Application No. 63/028,008 filed May 21, 2020 and U.S. Provisional Application No. 63/029,053 filed May 22, 2020, the entireties of which are incorporated fully herein by references.

BACKGROUND

The following description relates generally to a leakage detection system for medical devices, and more particularly to leakage detection system for ostomy devices.

An ostomy pouch system typically includes a pouch formed from opposing sidewalls defining an internal collection area, an inlet opening for receiving a stoma, and an ostomy appliance for attaching the pouch to a user. The ostomy appliance may include, for example, an ostomy barrier of a one-piece pouch system, which is attached to one of the pouch sidewalls proximate an inlet opening, a faceplate for a two-piece pouch system configured to releasably engage a pouch, and a barrier ring. The ostomy appliance may include a skin barrier material for adhering to and sealing against user's peristomal skin surrounding the stoma.

The ostomy appliance may be susceptible to ostomy effluent leakage, and the seal formed between the skin barrier material and the user may weaken. Often times, the user may be unaware of or cannot easily assess an extent of weakening in the seal. Thus, the user may not become aware of a weakened seal, and consequently, the ostomy effluent may leak through to an exterior of the ostomy appliance.

Accordingly, it is desirable to provide a leakage detection system for ostomy devices.

SUMMARY

In an embodiment, an ostomy device includes a proximal side configured for attachment to a user, a distal side opposite to the proximal side, and a leakage detection sensor having electrically conductive circuitry supported on a support layer. The leakage detection sensor is configured to detect ostomy effluent by detecting a change in resistance in the electrically conductive circuitry.

The support layer may be a skin barrier and the proximal side is a proximal side of the skin barrier. The leakage detection sensor may be configured to detect ostomy effluent by detecting a change in a resistance in the skin barrier. The leakage detection sensor may include includes at least one resistance sensor, wherein the at least one resistance sensor may be configured to detect a change in resistance.

The leakage detection sensor may be configured to determine a location of an ostomy effluent leak and may include a plurality of resistance sensors. The leakage detection sensor may include a ring-shaped body formed from a flexible printed circuit board and a plurality of resistance sensors arranged on the ring-shaped body.

The plurality of resistance sensors may be arranged in at least two rows. The resistance sensors arranged in a first row are closer to a center of the leakage detection sensor than the resistance sensors arranged in a second row. The plurality of resistance sensors may be arranged in at least two different quadrants of the ring-shaped body.

The leakage detection sensor may be configured to determine a location of an ostomy effluent leak by associating a signal indicating a change in resistance to a location of the resistance sensor generating the signal. The leakage detection sensor may be configured to track a progress of an ostomy effluent leak by associating a first signal indicating a change in resistance to a location of the resistance sensor generating the first signal and associating a second signal indicating a change in resistance to a location of the resistance sensor generating the second signal.

In an embodiment, the support layer may be a substrate and the leakage detection sensor may be disposed between a skin barrier and a backing layer, the leakage detection sensor may include at least one resistances sensor, and the proximal side may be a proximal side of the skin barrier.

The ostomy device may further include at least one wicking component configured to facilitate transport of the ostomy effluent toward the leakage detection sensor. The at least one wicking component may be configured to reduce a signal noise by filtering out at least some solid components in the ostomy effluent. The at least one wicking component may be configured to saturate at a threshold liquid volume, wherein the at least one resistance sensor may be configured to generate a consistent signal at or above the threshold liquid volume. The leakage detection sensor may be configured to generate an alarm when the consistent signal is received. The skin barrier may include at least one cut-out configured to contain the at least one wicking component.

The leakage detection sensor may include a plurality of resistance sensors formed of eight pairs of conductive traces arranged in two rows and in four quadrants of the ring-shaped body. The ostomy device may include eight wicking components, each of the wicking components configured and arranged to cover an adjacent conductive trace pair. The skin barrier may include eight cut-outs configured to contain the eight wicking components. The ostomy device may further include a backing layer. The leakage detection sensor may be arranged between the skin barrier and the backing layer.

In an embodiment, the leakage detection sensor may be a leak detection system configured to identify an ostomy effluent leakage event by detecting a change in resistance of a user's skin. The leak detection system may include at least one pair of electrodes arranged on a body-side surface of the skin barrier. Each of the at least one pair of electrodes is configured to measure resistance of a portion of user's skin adjacent the electrode pair. The body-side surface may be at the proximal side. The at least one pair of electrodes may be formed from a plurality of resistance sensors.

The leak detection system may be configured to identify an ostomy effluent leakage event by detecting a change in resistance of a user's skin resulting from a presence of ostomy effluent at an intersection between the skin barrier and the user's skin. The leak detection system may be configured to identify a skin inflammation event by detecting a change in resistance of a user's skin. The leak detection system may be configured to determine a location of an ostomy effluent leakage by associating a signal indicating a change in resistance to a location of the electrode pair generating the signal.

The leak detection system may be configured to track a progress of an ostomy effluent leakage by associating a first signal indicating a change in resistance to a location of an electrode pair generating the first signal and associating a second signal indicating a change in resistance to a location of an electrode pair generating the second signal. The leak detection system may include at least two pairs of electrodes arranged in at least two rows. The electrode pair arranged in a first row is closer to a center of the leak detection device than the electrode pair arranged in a second row. The at least two pairs of electrodes may be arranged in at least two different quadrants of the skin barrier.

In an embodiment, the skin barrier may be formed from a hydrocolloid adhesive. In an embodiment, the ostomy device may be an ostomy appliance. In an embodiment, the ostomy appliance may be a skin barrier ring. In an embodiment, the distal side may be configured to be attached to an ostomy pouch.

The ostomy device may further include an adhesive layer and a barrier-side layer and the proximal side may include a proximal side of the adhesive layer. The support layer is a substrate and the leakage detection sensor is a sensor layer disposed between the adhesive layer and the barrier-side layer. The barrier-side layer may be configured to be adhered to an ostomy appliance, and the distal side may include a distal side of the barrier-side layer. In an embodiment, the ostomy appliance may be a barrier of an ostomy pouch system.

In an embodiment, the ostomy device may further include a stoma passage extending through the adhesive layer, the sensor layer and the barrier-side layer. In an embodiment, the ostomy device may include a second adhesive layer disposed between the sensor layer and the barrier-side layer. In an embodiment, the barrier-side layer may be a film layer formed from a polymeric film material.

In an embodiment, the barrier-side layer may be a barrier-side adhesive layer formed from an adhesive material. The ostomy device may include a proximal side release liner removably disposed over the proximal side. The ostomy device may include a distal side release liner removably disposed over the distal side. In an embodiment, the distal side release liner may have a greater width than the proximal side release liner.

The sensor layer may include a sensor section and a connector section. The electrically conductive circuitry may be arranged in a pattern extending at least partially about the stoma passage at the sensor section. For example, the electrically conductive circuitry may be arranged in a circular pattern. The connector section may be an elongated section extending from the sensor section. The connector section may be flexible. In an embodiment, the connector section may extend beyond an outer periphery of the adhesive layer and/or the barrier-side layer in a direction radially outward from the stoma passage.

In an embodiment, the sensor layer further include an electrical connector. The electrically conductive circuitry may include a plurality of electrodes and/or conductive traces. The electrically conductive circuitry may be arranged at a plurality of different, radial distances from the stoma passage. The ostomy device may be an ostomy accessory configured for attachment to an ostomy appliance.

According to another aspect, an ostomy assembly may include an ostomy device, wherein the ostomy device is an ostomy accessory, and an ostomy pouch system having an ostomy appliance and an ostomy pouch. The distal side of the ostomy accessory may be adhered to a proximal side of the ostomy accessory.

The ostomy appliance may include a barrier having an adhesive material, and the ostomy pouch may be coupled to the barrier. The distal side of the ostomy accessory may be adhered to the proximal side of the adhesive material of the barrier.

According to another aspect, a leak detection system for a medical device may include at least one sensor configured to detect a leak and at least one wicking component. The at least one wicking component may be configured to facilitate transport of a leaking material to the sensor and facilitate consistent and reliable signal generation by the at least one sensor. The at least one wicking component may be configured to saturate at a threshold liquid volume. The at least one sensor may be configured to generate a consistent signal at or above the threshold liquid volume.

The at least one wicking component may be configured to filter out at least some solids in the leak material. The at least one wicking component may be configured to transport a particular component of a leak material to the at least one sensor for a selective leak detection. The at least one wicking component may include at least two zones. Each zone may be configured to transport the leaking material at a different flow rate.

Other objects, features, and advantages of the disclosure will be apparent from the following description, taken in conjunction with the accompanying sheets of drawings, wherein like numerals refer to like parts, elements, components, steps, and processes.

DETAILED DESCRIPTION

Figure 1:
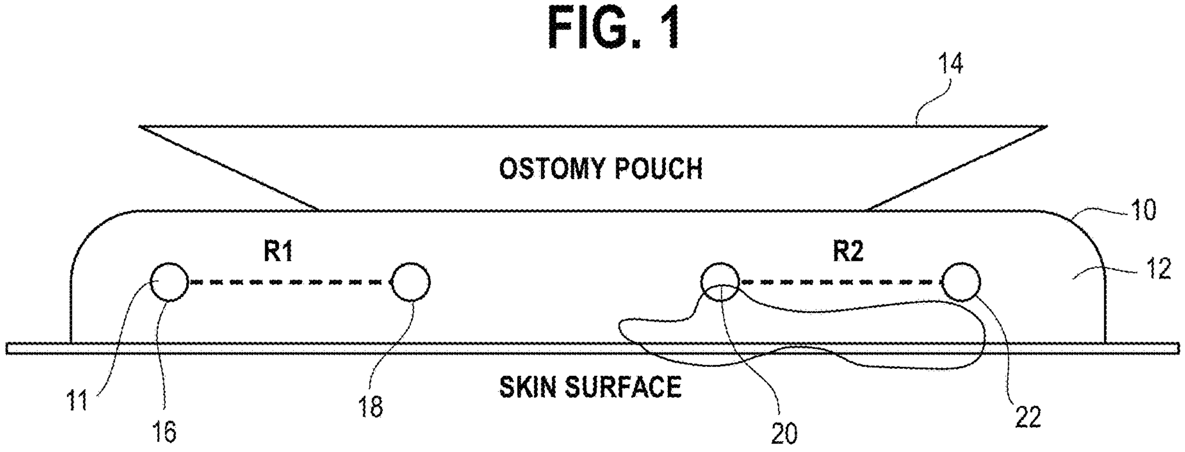
FIG. 1 is a schematic illustration of an ostomy appliance including a leakage detection system according to an embodiment.

While the present disclosure is susceptible of embodiment in various forms, there is shown in the drawings and will hereinafter be described one or more embodiments with the understanding that the present disclosure is to be considered illustrative only and is not intended to limit the disclosure to any specific embodiment described or illustrated.

According to embodiments herein, an ostomy leakage detection sensor may be embodied as or include, for example, a leakage detection system, a leakage detection device, a resistance sensor and/or a sensor layer. According to embodiments herein, an ostomy device may include the ostomy leakage detection sensor. The ostomy device may be embodied as, or include, for example, an ostomy appliance or an ostomy accessory.

According to an embodiment, an ostomy appliance may comprise a skin barrier material and may be configured as a faceplate assembly for a two-piece ostomy pouch system, an ostomy barrier for a one-piece ostomy pouch system, an ostomy skin barrier ring, and the like.

According to an embodiment, an ostomy accessory may be configured for attachment to an ostomy appliance, such as a barrier of the ostomy appliance.

According to an embodiment, an ostomy pouch system may include an ostomy appliance and an ostomy pouch. The ostomy accessory may be attached to the ostomy pouch system, for example, to a barrier of the ostomy pouch system.

According to an embodiment, an ostomy assembly may include, for example, an ostomy accessory, an ostomy appliance and an ostomy pouch.

According to an embodiment, the ostomy leakage detection sensor may generally include electrically conductive circuitry supported by a support layer. The electrically conductive circuitry may include, for example, electrodes, conductive traces and the like. The support layer may be a layer of material, such as a polymeric film layer, an adhesive layer, or other layer of material suitable for use in ostomy applications. The electrically conductive circuitry may be applied on the support layer, embedded in the support layer, or some combination thereof. In an embodiment, the electrically conductive circuitry may be a printed circuit formed using an electrically conductive ink.

The leakage detection sensor may be configured to detect ostomy effluent by detecting an electrical resistance and/or a change in electrical resistance in the electrically conductive circuitry. For example, in the event of ostomy effluent being introduced between spaced apart portions of the electrically conductive circuitry, for instance, during a leakage event, the electrical resistance between the spaced apart portions may decrease. Thus, the lower electrical resistance and/or decrease in electrical resistance detected by the leakage detection sensor may be indication of an ostomy effluent leakage event.

In an embodiment, the ostomy leakage detection sensor may further include, or be operably connected to, a controller. The controller may be configured to receive information, for example in the form of a signal, from the electrically conductive circuitry, process the received information, determine whether a leakage event has occurred, and/or provide a notification. The controller may also communicate with other devices, such as portable electronic devices, servers, wearable devices, and the like, using known wired and/or wireless communications.

The information received from the electrically conductive circuitry may be information indicative of a measured electrical resistance or measured change in electrical resistance. In different embodiments, the controller may store threshold values of electrical resistance or changes in electrical resistance and may compare the received information to one or more of the stored threshold values to determine whether a leakage event has occurred. The controller may also store position information of the electrically conductive circuitry and may determine, for example, a location and/or an extent of a leakage event based on, for example, the position information, the received information and the stored information.

The controller may generate a notification to be provided to a user based on the determination of whether a leakage event has occurred. The notification may include indications of whether a leakage event has occurred, the position of the leakage event, and/or the extent of the leakage event. The controller may include or be operably connected to an output module or device configured to provide the notification to a user. The output module or device may be, for example, a visual display, an audio speaker, a vibrating motor, and the like, to provide visual, audio and/or haptic notifications.

In an embodiment, the controller may be removably connected to the ostomy leakage detection sensor. For example, in an embodiment, the controller may be part of a wearable device or control unit that may be connected to and disconnected from the leakage detection sensor. In an embodiment, the controller may be wirelessly connected to the leakage detection sensor. The controller may be electrically connected to the electrically conductive circuitry. The controller may include, or be operably connected to, a power source configured to apply an electrical current to the electrically conductive circuitry. In an embodiment, a power supply may be included with the wearable device or included with the leakage detection sensor on the ostomy device.

In an embodiment, the controller may be a single controller or may include multiple controllers. The controllers may be located at different devices, such as the ostomy device, a wearable device, a portable electronic device, and the like, and may perform some or all of the operations described herein at one or more of the devices.

According to embodiments, the ostomy device may generally include a proximal, body-facing side configured to face toward the user, and a distal, pouch-facing side configured to face away from the user, for example, toward an ostomy pouch.

FIG. 1 is a schematic illustration of an ostomy appliance 10 comprising an ostomy leakage detection sensor 11 according to an embodiment. In an embodiment, the ostomy leakage detection sensor 11 may be a leakage detection system 11. The ostomy appliance 10 may comprise a skin barrier material 12 and may be configured as a faceplate assembly for a two-piece ostomy pouch system, an ostomy barrier for a one-piece ostomy pouch system, an ostomy skin barrier ring, and the like. In the embodiment of FIG. 1, the ostomy appliance 10 may be attached to an ostomy pouch 14.

The leakage detection system 11 may comprise electrically conductive circuitry, for example, one or more pairs of electrodes 16, 18, 20, 22, configured to measure electrical resistance between the pairs of electrodes to detect ostomy effluent leakage. The electrodes 16, 18, 20, 22 may be arranged on a support layer at body-side surface, a distal surface, or embedded in the ostomy appliance 10. In the embodiment of FIG. 1, the support layer may be the skin barrier material 12, and the electrodes 16, 18, 20, 22 may be embedded in the skin barrier material 12. In some embodiments, the ostomy appliance 10 may include at least one wicking component configured to direct ostomy effluent toward the electrodes 16, 18, 20, 22 to facilitate leak detection.

The electrodes 16, 18, 20, 22 may be electrically connected via a printed circuit or wiring to a controller (not shown) or a wireless transmitter configured to transmit information to a controller. In an embodiment, the controller may be a microcontroller. The controller may include a processor, a memory and a communication module operably connected to one another. The processor may be a microprocessor or other processing device configured to execute program instructions. The processor may be configured to control operations of the controller based on the program instructions. The memory may be a computer-readable medium, such as a non-transitory computer-readable medium. The program instructions may be stored in the memory. The communication module may be configured for wired and/or wireless communications. The communication module may be configured to transmit information to, and receive information from, other electronic devices, sensors, and the like.

In an embodiment, the controller may further include, or be operably connected to, for example, and input module configured to receive input from a user or sensor, an output module configured to output information to a user, and/or a power supply to provide electrical current to the electrically conductive circuitry.

In an embodiment, the controller may be configured to, for example, apply current to the electrodes, receive signals from the electrodes, process the signals, transmit the signals or processed signals to another electronic device, receive information from another electronic device or a user interface, and/or provide a notification or alert to a user based on the processed signals. In an embodiment, the controller may be implemented as a component of the ostomy appliance 10, for example, as part leakage detection system 11.

In an embodiment, the controller may be located at a single device, such as the ostomy appliance 10 and all operations of the controller may be carried out at the device. In another embodiment, the controller may be distributed across multiple devices, such as the ostomy appliance 10 and a portable electronic device. Components of the controller, such as those described above, may be located at one or more of the multiple devices, and operations of the controller, such as those described above, may be performed at one or more of the multiple devices.

In an embodiment, the leakage detection system 11 may be configured to determine a baseline resistance measurement R1 immediately after the ostomy appliance 10 is attached to a user. Alternatively, the baseline resistance measurement R1 may be determined during product development and preprogrammed in the leakage detection system 11. The leakage detection system 11 may be configured to detect a leak from a change in resistance across the ostomy appliance 10. In an embodiment, the leakage detection system 11 may be configured to detect a leak when ostomy effluent is absorbed by the skin barrier material 12 and/or by one or more wicking components in the ostomy appliance 10, which may increase the conductivity across the ostomy appliance, thereby reducing resistance R2. For example, the leakage detection system 11 may be configured to detect a leak when ostomy effluent, which may contain aqueous salts, bridges one or more pairs the electrodes 16, 18, 20, 22.

Figure 2:
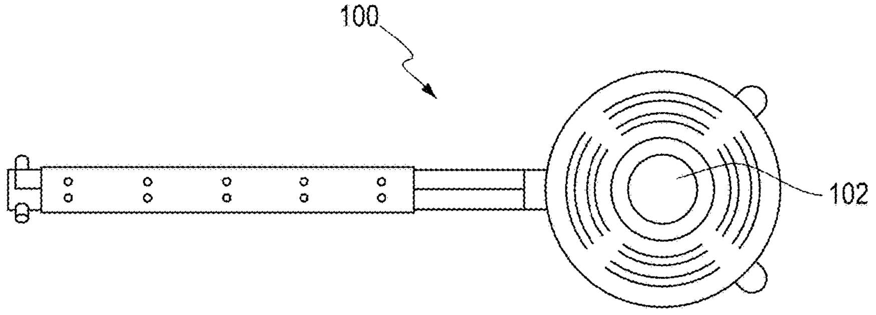
FIG. 2 is a schematic top view of an ostomy appliance including a leakage detection device according to an embodiment.
Figure 3:
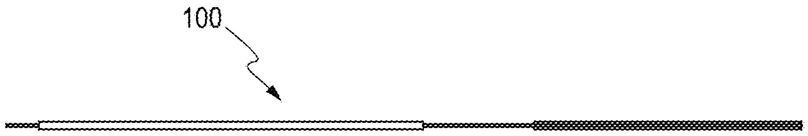
FIG. 3 is a schematic side view of the ostomy appliance of FIG. 2.
Figure 4:
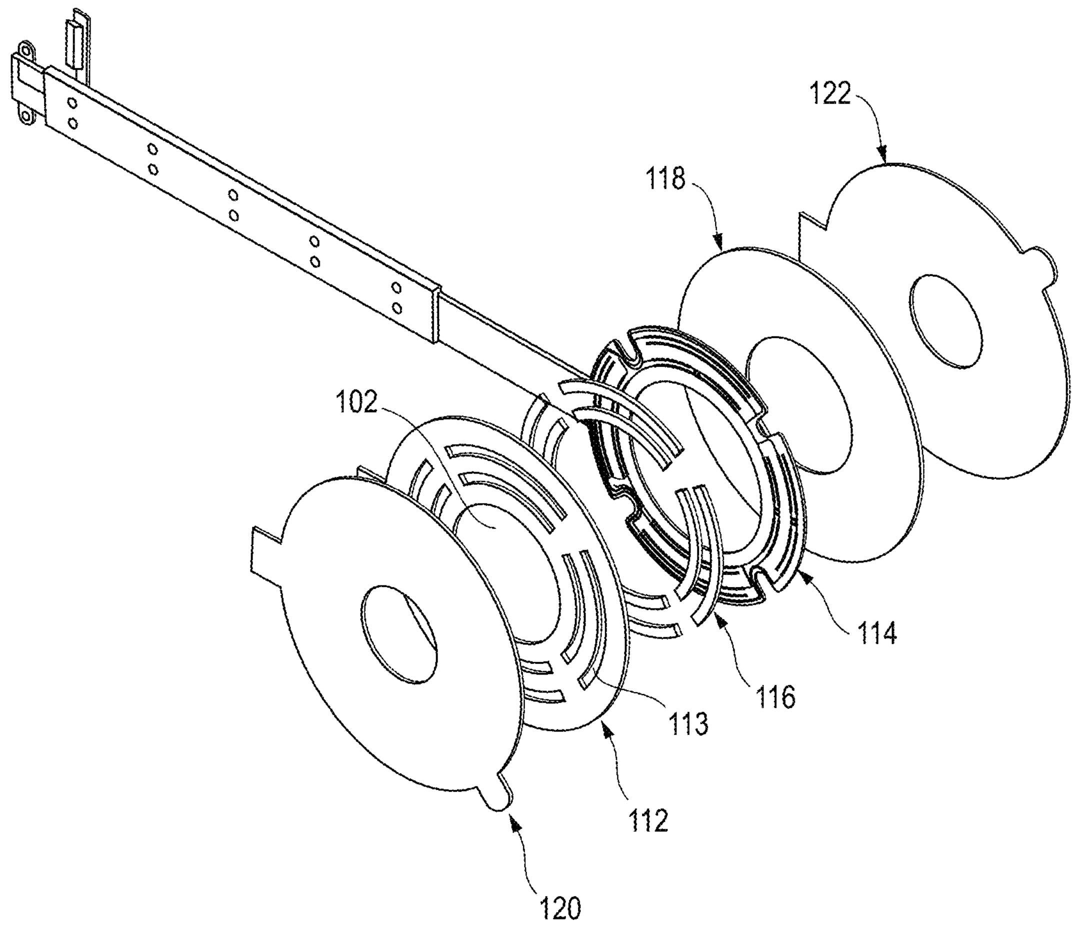
FIG. 4 is an exploded view of the ostomy appliance of FIG. 2.

Referring to FIGS. 2-4, an ostomy appliance 100 having an ostomy leakage detection sensor according to an embodiment is illustrated. In an embodiment, the ostomy leakage detection sensor may be a leakage detection device 114. As best shown in FIG. 4, the ostomy appliance 100 may generally comprise a skin barrier 112, the leakage detection device 114, a plurality of wicks 116, and a backing layer 118.

In an embodiment, the ostomy appliance 100 may be configured as an ostomy skin barrier ring including an opening 102 for receiving user's stoma. The ostomy appliance 100 may be configured to have a relatively thin profile (FIG. 3) to provide flexibility sufficient for use with an ostomy pouch.

The skin barrier 112 may be provided on a body side of the ostomy appliance 100 for attaching the ostomy appliance 100 to user's skin. The skin barrier 112 may be formed from a suitable medical grade adhesive, such as a hydrocolloid adhesive. The backing layer 118 may be provided on a distal side of the ostomy appliance 100. The backing layer 118 may be formed from a soft, flexible material that is generally soft and non-irritable to the user's skin, such as an adhesive, nonwoven or foam material. In an embodiment, the backing layer 118 may be formed from a malleable hydrocolloid. For example, the backing layer 118 may be formed from the same hydrocolloid adhesive used to form the skin barrier 112. In such an embodiment, release liners 120, 122 may be provided to cover the skin barrier 112 and the backing layer 118.

Figure 5A:
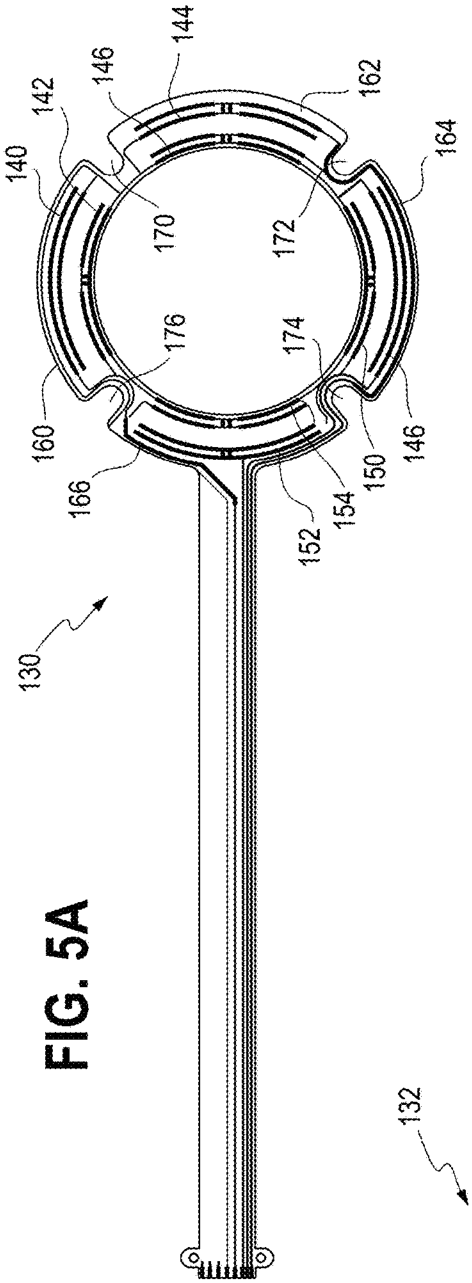
FIG. 5A is a schematic illustration of a top layer of the leakage detection device of the ostomy appliance of FIG. 2.
Figure 5B:
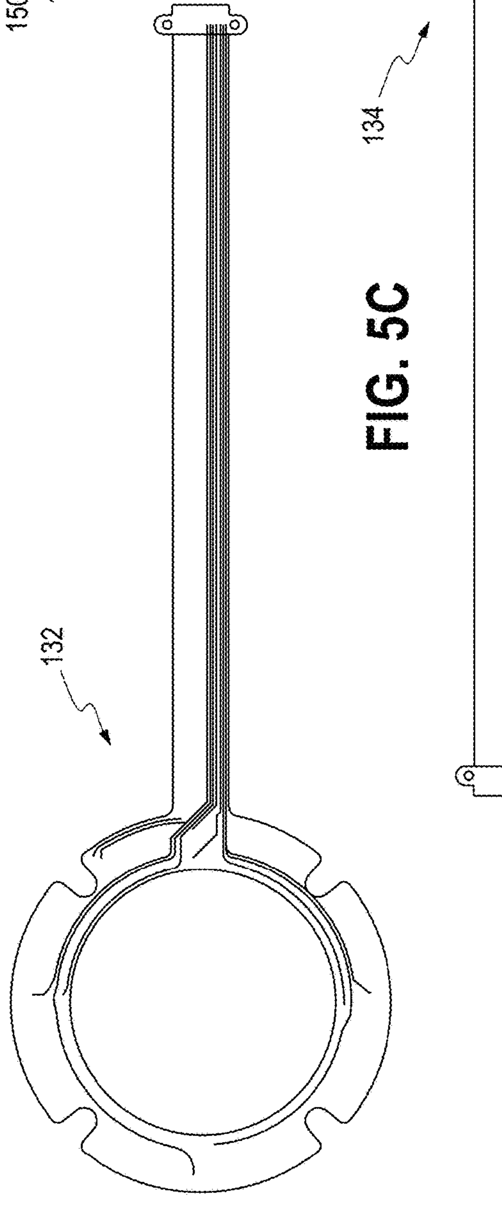
FIG. 5B is a schematic illustration of a bottom layer of the leakage detection device of the ostomy appliance of FIG. 2.
Figure 5C:
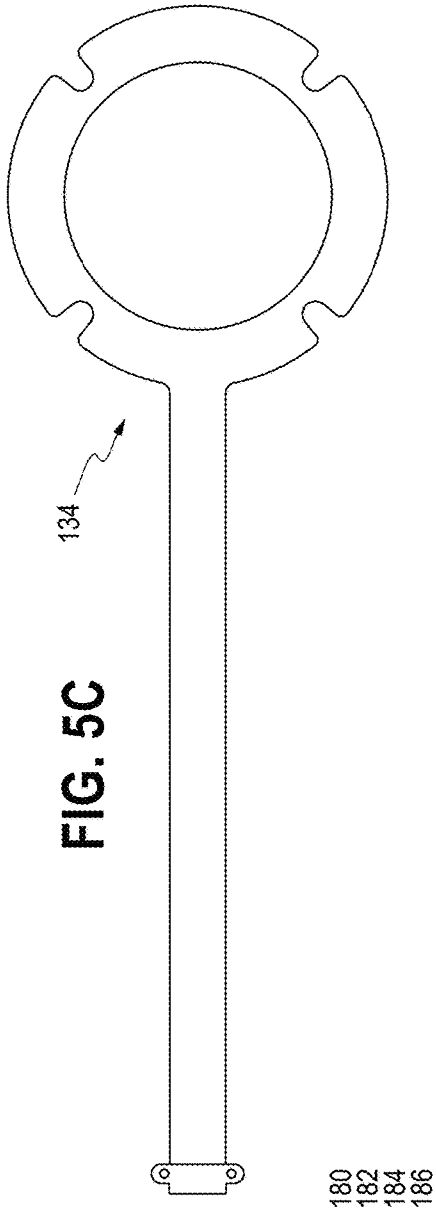
FIG. 5C is a schematic illustration of a stiffener layer of the leakage detection device of the ostomy appliance of FIG. 2.

The leakage detection device 114 may comprise a flexible printed circuit board (PCB) including an electrically conductive circuit having a plurality of resistance sensors. In an embodiment, the leakage detection device 114 may comprise a top layer 130 (FIG. 5A), a bottom layer 132 (FIG. 5B), and a stiffener layer 134 (FIG. 5C). The top layer 130 may be arranged on the skin barrier 112 facing side of the leakage detection device 114, while the bottom layer 132 may be arranged on the backing layer 118 facing side. The stiffener layer 134 may be arranged between the top layer 132 and the bottom layer 132. The plurality of resistance sensors 140, 142, 144, 146, 148, 150, 152, 154 may be provided on a PCB having a generally ring-shaped body including notches 170, 172, 174, 176, which may divide the PCB into four quadrants 160, 162, 164, 166.

The plurality of resistance sensors may be configured and arranged for consistent and accurate signal generation and for location detection of a leak. In an embodiment, the leakage detection device may comprise eight pairs of resistance sensors 140, 142, 144, 146, 148, 150, 152, 154, which may be arranged on the top layer 130 as shown in FIG. 5A. The eight pairs of resistance sensors 140, 142, 144, 146, 148, 150, 152, 154 may be formed of eight pairs of arc-shaped conductive traces, which may be arranged in four quadrants 160, 162, 164, 166 in two rows. In such an embodiment, the first row sensors 142, 146, 150, 154 may be arranged closer to an inner periphery of the leakage detection device 114 the second row sensors 140, 144, 148, 152. In some embodiments, the leakage detection device 114 may comprise two or more different types of sensors. For example, the leakage detection device 114 may comprise at least one set of resistance sensors and at least one self-heating thermistor.

The pairs of resistance sensors 140, 142, 144, 146, 148, 150, 152, 154 may be configured and arranged for a location detection of a leak. For example, the leakage detection device 114 may be configured to determine a location of a leak by associating signals indicating a change in resistance to the location of the sensors that generated the signals. The leakage detection device 114 may also be configured to track a progress of a leak by tracking the locations of the sensors generating signals indicating a change in resistance. For example, a signal indicating a change in resistance may be first generated by the pair of sensors 142, and subsequently also generated by the pair of sensors 146, which may indicate a leak progressing from the first quadrant 160 to the second quadrant 162. In another example, a signal indicating a change in resistance may be first generated by the pair of sensors 142, and subsequently also generated by the pairs of sensors 140, which may indicate a leak progressing toward an outer periphery of the leakage detection device 114.

In some embodiments, the leakage detection device 114 may be configured with a threshold resistance value for a user notification. The leak detection device 114 may also be configured to monitor resistance values measured by the resistance sensors and use the data in algorithms to predict a potential leak or generate various information about a leak. For example, the leakage detection device 114 may be configured to analyze resistance date to predict a wear time of the ostomy appliance 100 before a leak reaches a critical threshold.

In other embodiments, the leakage detection device 114 may comprise less than eight pairs of resistance sensors or more than eight pairs of resistance sensors, which may be configured and arranged to detect and inform a leak to a user. In some embodiments, the leakage detection device 114 may include a single type of sensor or more than two types of sensors.

Figure 6:
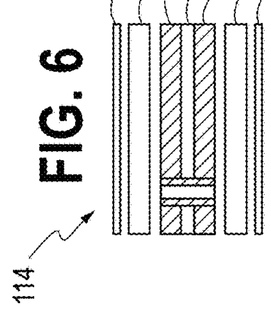
FIG. 6 is a schematic cross-sectional view of the leakage detection device of the ostomy appliance of FIG. 2.

FIG. 6 is a schematic cross-sectional view of the leakage detection device 114 according to an embodiment. In this embodiment, the top layer 130 may comprise conductive traces 180 printed on a support layer 182 to form the pairs of resistance sensors 140, 142, 144, 146, 148, 150, 152, 154. In an embodiment, and as shown in FIG. 6, the support layer may be a first substrate 182. The stiffener layer 134 may comprise a flexible polymeric film 186 arranged between copper layers 184, 188. The bottom layer 132 may comprise a second substrate 190 and circuits 192 printed thereon.

Each of the first and second substrates 182, 190 may be formed from a suitable flexible polymeric material, such as a polyimide film. The first and second substrates 182, 190 may be formed from a same flexible polymeric material or different flexible polymeric materials. Each of the first and second substrates 182, 190 may have a thickness of about 0.5 mil to about 3 mil, preferably, about 1 mil to about 2 mil, and more preferably about 1.5 mil. In an embodiment, each of the first and second substrates 182, 190 may be formed from a coverlay film having a thickness of about 1.3 mil and comprising a polyimide film coated with an acrylic adhesive on one side, such as PYRALUX® FR7013 available from Dupont.

The stiffener layer 134 may comprise a first copper layer 184, a flexible laminate 186, and a second copper layer 188. The flexible laminate 186 may have a thickness of about 0.25 mil to about 3 mil, preferably about 0.5 mil to 2 mil, and more preferably about 1 mil. Each of the copper layers 184, 188 may have a thickness of about 0.5 mil to about 3 mil, preferably about 1 mil to 2 mil, and more preferably about 1.3 mil. The flexible laminate 186 may be formed from a suitable flexible circuit board material having a thickness of about 1 mil and comprising a polyimide substrate laminated between copper foil layers, such as FELIOS® RF775 available from Panasonic.

In an embodiment, the ostomy appliance 100 may comprise a plurality of wicks 116 configured to facilitate transport of ostomy effluent toward the resistance sensors 140, 142, 144, 146, 148, 150, 152, 154. The plurality of wicks 116 may be configured to transport components of ostomy effluent, for example, moisture, liquid, and some solid dissolved or dispersed in liquid, which may bridge one or more pairs of the resistance sensors 140, 142, 144, 146, 148, 150, 152, 154 to cause a change in resistance. In the embodiment of FIG. 4, the plurality of wicks 116 may comprise eight arc-shaped wicks arranged over the eight pairs of similarly shaped resistance sensors 140, 142, 144, 146, 148, 150, 152, 154, wherein each of the eight wicks may be configured to cover a corresponding resistance sensor. The skin barrier 112 may be provided with eight arc-shaped cut-outs 113 configured to contain the plurality of wicks 116. Such a configuration may allow ostomy effluent to contact the plurality of wicks 116 directly to facilitate leak detection.

In an embodiment, the plurality of wicks 116 may be configured to facilitate consistent and reliable signal generation by leak detection sensors. For example, the plurality of wicks 116 may be configured to filter larger solid components in ostomy effluent and transport moisture and liquid components to the sensors, which may reduce signal noise. In another example, the plurality of wicks 116 may be configured to have a predetermined liquid saturation threshold, above which the sensors may generate the same signal. The threshold saturation volume of the wicks 116 may be adjusted by changing a wick material or changing the geometry of the wicks 116. In an embodiment, the plurality of wicks 116 may be configured to saturate at a predetermined threshold leak volume, above which may be a concern to a user. In such an embodiment, the leakage detection system 114 may be configured to alert the user at or above the threshold point, such that false or premature alarms, such as small leaks that may not pose a risk to the user or a change in resistance triggered by sweat, may be reduced. In an embodiment, the plurality of wicks 116 may be configured for a selective detection. For example, the plurality of wicks 116 may be configured to transport certain components of ostomy effluent that are not contained in other materials, such as sweat, such that selective detection of ostomy effluent leak may be enabled.

The plurality of wicks 116 may be formed from a suitable wicking material, such cellulose materials, paper-like materials and the like. In an embodiment, the plurality of wicks 116 may be formed from an open-cell foam.

In other embodiments, the ostomy appliance 100 may include less than eight wicks or more than eight wicks. In an embodiment, the ostomy appliance 100 may include a single wick configured and arranged to facilitate transport of ostomy effluent toward one or more sensors. In some embodiments, the single wick may be configured to have varying flow rates in one or more portions thereof. For example, the single wick may be compressed, thinned or otherwise altered in one or more portions to provide dead zones or reduce flow rate zones, such that the single wick may function similar to a plurality of wicks. In an embodiment, portions of the wick may be impregnated with a substance to block flow, such as wax, to create dead zones. In some embodiments, the ostomy appliance 100 may include one or more wicks configured and arranged to completely encircle the opening 102 to ensure that ostomy effluent contacts the one or more wicks as a leak propagates outwardly from the stoma.

The ostomy appliance 100 may also include an electrically-attached controller (not shown) configured to receive signals from the resistance sensors, analyze the received signals, and provide an alert or notification to a user of a potential leak via audio, vibrational, optical or tactile alerts, based on the received signals. The received signals may be indicative of a detected resistance or change in resistance.

In some embodiments, the ostomy appliance 100 may be provided with a wearable device including the controller. The wearable device may also include a power supply, such as a battery, and a wireless transceiver operably connected to the controller. The wearable device may be removably connected to the ostomy appliance 100, for example, by way of friction fit, interference fit, clamping, mechanical interlock, or other suitable fastening mechanism. In an embodiment, the wearable device may be removably connected to a portion of the leakage detection device 114.

In an embodiment, the electrically-attached controller may be same as the controller described above. In an embodiment, the electrically-attached controller may include some or all of the components of the controller described above and perform some or all of the operations of the controller described above. For example, the electrically-attached controller may include a processor, a computer-readable storage medium configured to store program instructions to be executed by the processor, and a communication module configured to transmit and/or receive information. In an embodiment, the processor, computer-readable storage medium and communication module may be operably connected to one another by a bus.

In an embodiment, the communication module may include a wired communication interface and/or a wireless communication interface configured to facilitate transmission and/receipt of information according to known, suitable communication protocols. In an embodiment, the communication interface may include the wireless transceiver. The wireless transceiver may be configured for wireless communications according to known wireless communication standards and protocols and may communicate over known communication networks, such as personal area networks, wireless local area networks, metropolitan area networks and wide area networks. Accordingly, the wireless transceiver may be configured for various wireless communications including, but not limited to, Bluetooth, Bluetooth Low Energy, Near-Field Communication, WiFi, WiMax, cellular LTE or other cellular radio communications. In one embodiment, the wireless transceiver may be a Bluetooth enabled microchip.

In an embodiment, the user interface may include or be operably connected to, for example, one or more of a display device, an audio device, a haptic device, and/or a user input device. In an embodiment, the user interface may be part of an input module for receiving information from a user or sensor or an output module to output information to a user.

The controller may further include a power supply such as a battery, configured for applying electrical current to the leakage detection system 11. In another embodiment, the controller may be operably connected to a power supply and may control operations of power supply.

In one embodiment, the wearable device may include one or more output devices operably connected to the controller, such as a visual indicator, an audio indicator, or both. Alternatively, or in addition, other output devices may be envisioned as well, such as a vibrating indicator. The visual indicator may include, for example, a light emitting diode (LED) or a display, such as a liquid crystal display (LCD).

In one embodiment, the ostomy appliance 100 may be communicatively coupled to a personal notification device. The personal notification device may be communicatively coupled to the wearable device over a wireless communication interface via the wireless transceiver. In one embodiment, the personal notification device may be a mobile communication device, such as a smartphone or other mobile phone. Alternatively, or in addition, the personal notification device may be another mobile communication device, a portable electronic device, or other electronic device configured for communication, directly or indirectly, with the wearable device. Such devices may include, but are not limited to, tablets, laptop computers, desktop computers, smart speakers, connected wearable accessories such as fitness trackers, smart watches and the like, smart televisions, personal digital assistants and the like. In an embodiment, the personal notification device may include the controller. In an embodiment, the controller may include components at the ostomy appliance, for example, at the wearable device, and the personal notification device. In an embodiment, separate controllers of the type described herein may be located at the ostomy appliance, for example, at the wearable device, and the personal notification device and may be configured to communicate with one another.

In one embodiment, the wearable device may be paired, synced, or otherwise communicatively connected to the personal notification device with a known pairing or syncing operation, which may be initiated, for example, by operation of a switch.

Figure 7:
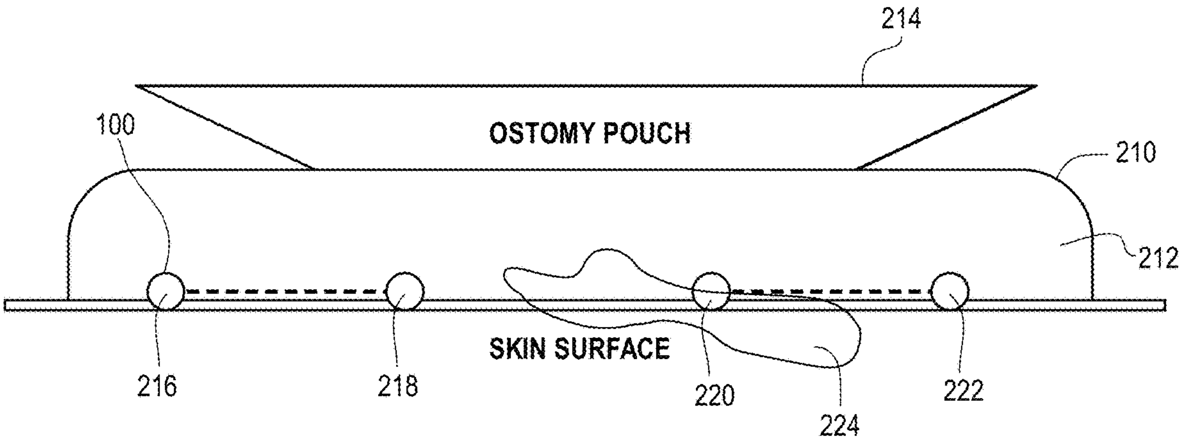
FIG. 7 is a schematic illustration of an ostomy appliance including a leak detection system according to an embodiment.

FIG. 7 is a schematic illustration of an ostomy appliance 210 comprising an ostomy leakage detection sensor 211 according to an embodiment. In an embodiment, the ostomy leakage detection sensor 211 may be a leakage detection system 211. The ostomy appliance 210 may comprise a skin barrier 212 and may be configured as a faceplate assembly for a two-piece ostomy pouch system, an ostomy barrier for a one-piece ostomy pouch system, an ostomy skin barrier ring, and the like. In the embodiment of FIG. 7, the ostomy appliance 210 may be attached to an ostomy pouch 214. The leak detection system 211 may comprise electrically conductive circuitry, for example, one or more pairs of electrodes 216, 218, 220, 222, wherein each pair of electrodes is configured to measure electrical conductance or resistance across a portion of user's skin. The electrodes 216, 218, 220, 222 may be arranged on a support layer on a body-side surface of the ostomy appliance 210 at a distance apart from each other in pairs and in contact with user's skin. In an embodiment, the support layer may be the skin barrier 212. The leak detection system 211 may be configured to detect and notify an ostomy effluent leakage event using the electrical conductance or resistance of user's skin measured by the electrode pairs.

In the embodiment of FIG. 7, the leak detection system 211 may include at least two pairs of electrodes comprising a first pair 216, 218 and a second pair 220, 222. In an embodiment, multiple pairs of electrodes may be arranged at various locations on the body-side surface of the ostomy appliance 210 to detect ostomy effluent leakage. For example, the multiple electrode pairs may be arranged to surround the stoma.

In an embodiment, each of the electrode pairs 216, 218, 220, 222 may be configured to measure a resistance across a portion of user's skin adjacent the corresponding electrode pair, for example, resistance R1 measured by a first electrode pair 216, 218 and resistance R2 measured by a second electrode pair 220, 222 in FIG. 7. The leak detection system 211 may be configured to identify a leakage event from a change in resistance measured by a pair of electrodes, which may be triggered by the presence of ostomy effluent at an interface between user's skin and the ostomy appliance 210. In the embodiment of FIG. 7, the leak detection system 211 may be configured to identify a leakage event from a change in resistance measured by the second electrode pair 220, 222 triggered by the presence of ostomy effluent 224. In some embodiments, the leak detection system 211 may be configured to identify a location of leakage by determining the location of the electrode pair that measured the leakage event triggering resistance change.

The resistance or conductivity of user's skin may be affected by various factors, such as humidity, temperature, sweat gland activity, sympathetic nervous system activity, inflammation response, hydration, etc. In an embodiment, the leak detection system 211 may be configured to identify a skin inflammation event from a change in resistance measured by an electrode pair at a corresponding portion of user's skin resulting from an inflammatory response of user's skin being exposed to ostomy effluent. In some embodiments, the leak detection system 211 may be configured to adjust and individualize identification of leak and/or inflammation events by analyzing a user's skin resistance measurement data. For example, the leak detection system 211 may be configured to collect and analyze user's historical data and utilize machine learning to filter out noise or adjust and individualize a response for a user. The electrodes 216, 218, 220, 222 may be electrically connected to a controller (not shown) via a printed circuit or wiring or a wireless transmitter. The controller may be configured to send power to the electrodes, receive signals from the electrodes, process the signals, and transmit the processed signals to notify a user. In an embodiment, the controller may be the same as any of the controllers described in other embodiments herein. In an embodiment, the controller may include one or more of components of the controllers described herein and may perform one or more of the functions of the controllers described herein.

In an embodiment, the ostomy appliance 210 may be configured as an ostomy skin barrier ring including an opening (not shown) for receiving user's stoma. The skin barrier 212 may be provided on a body side of the ostomy appliance 210 for attaching the ostomy appliance 210 to user's skin. The skin barrier 212 may be formed from a suitable medical grade adhesive, such as a hydrocolloid adhesive. The ostomy appliance 210 may also include a backing layer provided on a distal side of the ostomy appliance 210, which may be formed from a soft, flexible material that is generally soft and non-irritable to the user's skin, such as an adhesive, a polymeric film, a nonwoven, a foam, and the like. The electrode pairs 216, 218, 220, 222 may be formed from plurality of resistance sensors that are configured and arranged for consistent and accurate signal generation and for location detection of a leak.

In an embodiment, the leak detection system 211 may include at least two pairs of electrodes arranged in at least two rows, wherein the electrode pair arranged in a first row are closer to a center of the ostomy appliance 210 than the electrode pair arranged in a second row. The at least two pairs of electrodes may be arranged in at least two different quadrants of the skin barrier 212. In an embodiment, the leak detection system 211 may be configured to determine a location of a leakage by associating signals indicating a change in resistance to the location of the electrode pair that generated the signals. The leak detection system 211 may also be configured to track a progress of a leak by tracking the locations of the electrode pairs generating signals indicating a change in resistance.

In some embodiments, the leak detection system 211 may be configured with a threshold resistance value for a user notification. The leak detection system 211 may also be configured to monitor resistance data measured by the electrode pairs and use the data in algorithms to predict a potential leak or generate various information about a leak. For example, the leak detection system 211 may be configured to analyze resistance date to predict a wear time of the ostomy appliance 210 before a leak reaches a critical threshold.

In an embodiment, the ostomy appliance 210 may include an electrically-attached controller (not shown) configured to analyze signals generated by the electrode pairs and alert a user of a potential leak via audio, vibrational, optical or tactile alerts. In some embodiments, the ostomy appliance 210 may be provided with a wearable device (not shown) including a controller, a power supply, such as a battery, and a wireless transceiver. The wearable device may be removably connected to the ostomy appliance 210, for example, by way of friction fit, interference fit, clamping, mechanical interlock, or other suitable fastening mechanism.

The controller may be any of the controllers described herein. In an embodiment, the controller may be a microcontroller. In an embodiment, the controller may include a processor, a memory and a communication module operably connected to one another. The processor may be a microprocessor or other processing device configured to execute program instructions. The processor may be configured to control operations of the controller based on the program instructions. The memory may be a computer-readable medium, such as a non-transitory computer-readable medium. The program instructions may be stored in the memory. The communication module may be configured for wired and/or wireless communications. The communication module may be configured to transmit information to, and receive information from, other electronic devices, sensors, and the like.

In an embodiment, the controller, for example, the communication module, may include a wireless transceiver. In an embodiment, a wireless transceiver may be configured to communicate with the controller. The wireless transceiver may be configured for wireless communications according to known wireless communication standards and protocols and may communicate over known communication networks, such as personal area networks, wireless local area networks, metropolitan area networks and wide area networks. Accordingly, the wireless transceiver may be configured for various wireless communications including, but not limited to, Bluetooth, Bluetooth Low Energy, Near-Field Communication, WiFi, WiMax, cellular LTE or other cellular radio communications. In an embodiment, the wireless transceiver may be a Bluetooth enabled microchip.

In an embodiment, the wearable device may include one or more output devices or modules operably connected to the controller, such as a visual indicator, an audio indicator, or both. Alternatively, or in addition, other output devices may be envisioned as well, such as a vibrating indicator. The visual indicator may include, for example, a light emitting diode (LED) or a display, such as a liquid crystal display (LCD).

In an embodiment, the ostomy appliance 210 may be communicatively coupled to a personal notification device. The personal notification device may be communicatively coupled to the wearable device over a wireless communication interface via the wireless transceiver. In an embodiment, the personal notification device may be a mobile communication device, such as a smartphone or other mobile phone. Alternatively, or in addition, the personal notification device may be another mobile communication device, a portable electronic device, or other electronic device configured for communication, directly or indirectly, with the wearable device. Such devices may include, but are not limited to, tablets, laptop computers, desktop computers, smart speakers, connected wearable accessories such as fitness trackers, smart watches and the like, smart televisions, personal digital assistants and the like.

In an embodiment, the wearable device may be paired, synced, or otherwise communicatively connected to the personal notification device with a known pairing or syncing operation, which may be initiated, for example, by operation of a switch.

Figure 8:
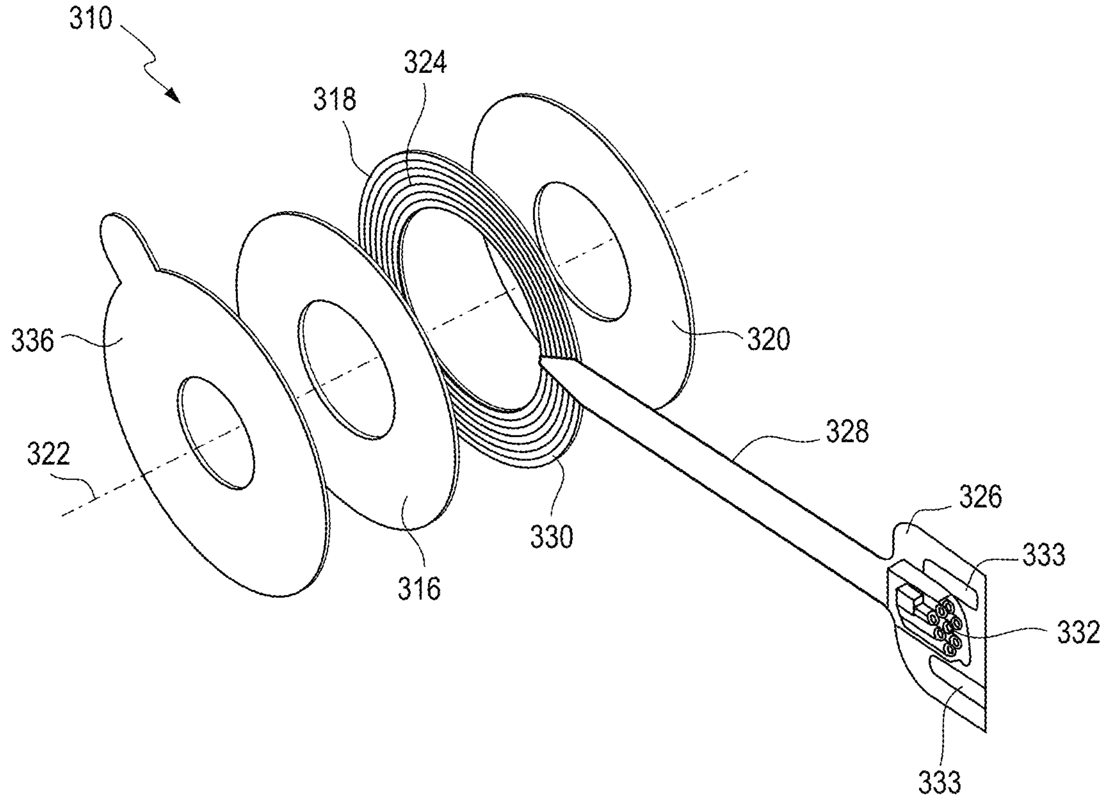
FIG. 8 is an exploded view illustrating an example of an ostomy accessory according to an embodiment.
Figure 9:
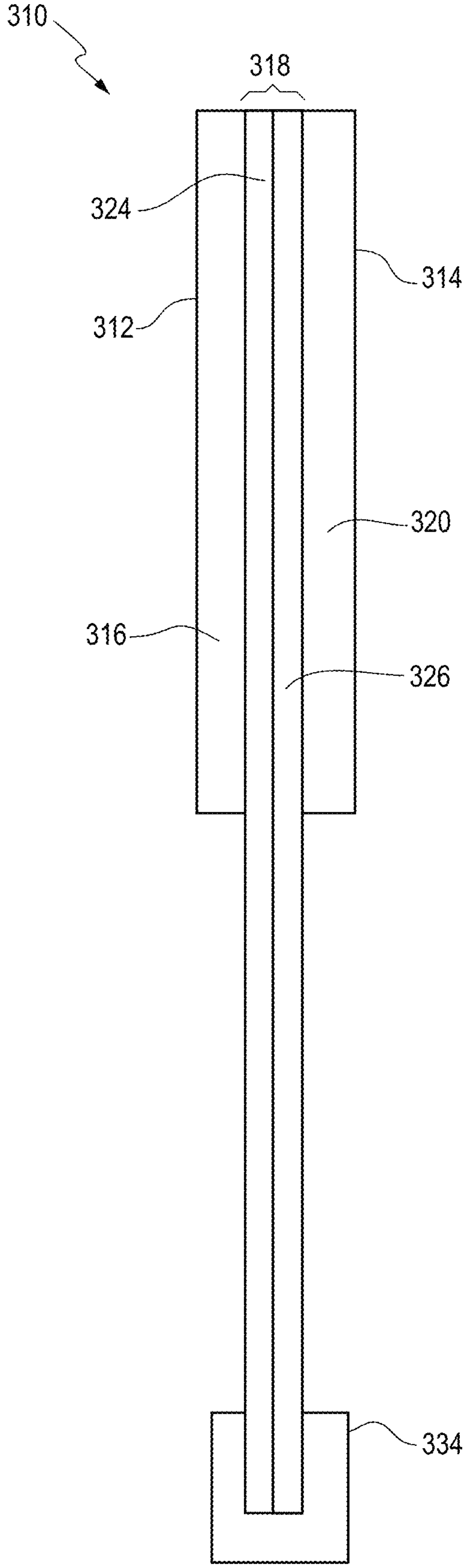
FIG. 9 is a diagram schematically illustrating a side view of an ostomy accessory according to an embodiment.

FIG. 8 is an exploded view illustrating an example of an ostomy accessory 310 according to an embodiment. FIG. 9 is a diagram schematically illustrating a side view of the ostomy accessory 310 according to an embodiment. Referring to FIGS. 8 and 9, the ostomy accessory 310 may include, for example, an ostomy leakage detection sensor and may be configured to be attached to an ostomy pouch system. The ostomy accessory 310 may have a proximal or body-facing side 312 and a distal or barrier-facing side 314 (FIG. 9). In an embodiment, the ostomy accessory 310 may include a first adhesive layer 316, a sensor layer 318 and a barrier-side layer 320. A stoma passage 322 may extend through the ostomy accessory 310 and may be configured to receive a portion of a stoma and/or stomal effluent discharged from the stoma. The stoma passage 322 may be formed by respective openings extending through individual layers of the ostomy accessory 310.

Each layer 316, 318, 320 of the ostomy accessory 310 has a proximal side and a distal side. In use, with the ostomy accessory 310 attached to a patient, the respective proximal sides generally face toward the patient and the respective distal sides generally face away from the patient.

The first adhesive layer 316 may be disposed at the body-facing side 312 of the ostomy accessory 310. In an embodiment, the proximal side of the first adhesive layer 316 may form at least a portion of the body-facing side 312 of the ostomy accessory 310. The proximal side of the first adhesive layer 316 may be configured to adhere to peristomal skin surfaces of the patient and seal against stomal fluid leakage around the stoma. In an embodiment, the first adhesive layer 316 may be formed from a medical-grade pressure sensitive adhesive that can adhesively secure the ostomy accessory 310 to a patient's peristomal skin surfaces. In an embodiment, the first adhesive layer 316 may include a hydrocolloid.

Figure 10:
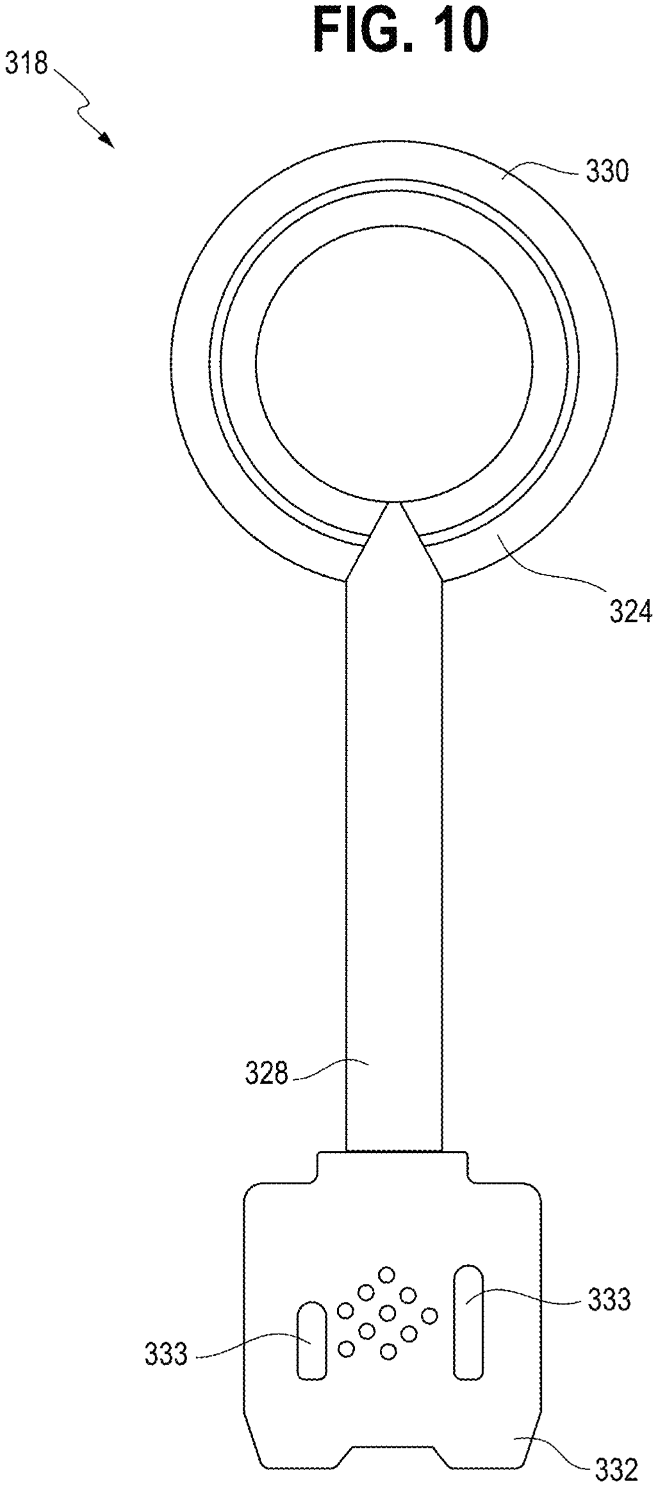
FIG. 10 is a plan view illustrating a sensor layer of the ostomy accessory according to an embodiment.

FIG. 10 is a plan view illustrating the sensor layer 318 according to an embodiment. In an embodiment, the sensor layer 318 may be the ostomy leakage detection sensor. Referring to FIGS. 8-10, the sensor layer 318 may include electrically conductive circuitry 324, such as a plurality of electrodes, conductive traces or the like. The electrically conductive circuitry 324 may be disposed on a support layer, such as substrate 326. In an embodiment, the sensor layer 318 may include a connector section 328 and a sensor section 330. The electrically conductive circuitry 324 may be arranged in a predetermined pattern at the sensor section 330. For example, the electrically conductive circuitry 324 may be arranged generally in a circular or semi-circular pattern. Other suitable patterns are envisioned as well, such as an oval or oblong pattern, or other closed or substantially closed loop pattern. The electrically conductive circuitry 324 at the sensor section 330 may be arranged at one or more radial distances from the stoma passage 322. For example, the electrically conductive circuitry 24 may be arranged at a plurality of different, radial distances from the stoma passage 322.

In an embodiment, the connector section 328 may generally be formed as an elongated section extending from the sensor section 330. For example, the electrically conductive circuitry 324 may extend along the elongated section. In an embodiment, the connector section 328 may be flexible along at least a portion of its length such that it may be folded or wrapped. In an embodiment, the connector section 328 may extend beyond an outer periphery of the adhesive layer 318 and/or the barrier-side layer 320 in a direction radially outward from the stoma passage 322.

The ostomy accessory 310 may further include an electrical connector 332. The electrical connector 332 may be electrically connected to the electrically conductive circuitry 324. The electrical connector may be disposed on the connector section 328. The electrical connector 332 may include an externally accessible portion configured for electrical connection to an external device, such as a control unit 334 (FIG. 9). The control unit 334 may be, for example, a wearable device of the type described above, and may include a controller according to any of the embodiments above. In this manner, the electrical connector 332 may provide an electrical connection between the control unit 334 and the electrically conductive circuitry 324. The externally accessible portion of the electrical connector 332 may be any suitable electrical interface for forming an electrical connection between two electrical components, such as one or more electrically conductive contacts, pins, and the like.

The electrical connector 332 may also include one or more alignment members 333. The one or more alignment members 333 are configured to engage corresponding alignment members (not shown) of the control unit 334 to indicate suitable positioning of the electrical connector 332 relative to the control unit 334 for providing the electrical connection. In an embodiment, the one or more alignment members 333 of the electrical connector 332 may be an opening, recess or slot. The corresponding alignment members (not shown) of the control unit 334 may be one or more projections (not shown) configured for receipt in the opening, recess or slot of the electrical connector 332.

The control unit 334 (FIG. 9) may be selectively and removably electrically connected to the electrical connector 332. For example, the control unit 334 may include a corresponding electrical connector (not shown) for interfacing with the electrical connector 332. The control unit 334 may be removably connected to the electrical connector 332 using a known, suitable mechanical fastener, such as a spring-load clip, mechanical interlock, clamp, interference fit, and the like, including combinations thereof. Alternatively, the control unit 334 may be integrated with the sensor layer 318.

The control unit 334, for example via the controller, may be configured to provide an electrical current to the electrically conductive circuitry 324 and detect a change in electrical resistance in the electrically conductive circuitry 324. For example, leakage of stomal effluent from the stoma passage 322 outward into or along the first adhesive layer 316, may cause electrical resistance between, for example, a pair of electrodes of the electrically conductive circuitry to decrease. The control unit 334 may detect the decrease in electrical resistance and determine that a leak is occurring based on the decreased electrical resistance. In an embodiment, the control unit 334, via the controller, may be configured to determine a location of the change in electrical resistance. The control unit 334 may be further configured to provide a notification or alert indicating that a leak has been detected and/or a location of the leak. The notification or alert may be, for example, an audible, visible, or haptic alert, or a combination thereof. The control unit 334 may also be configured for wired and/or wireless communication with other electronic devices, such as a smart phone and the like.

In an embodiment, the barrier-side layer 320 may be a film layer formed from a polymeric film material. In an embodiment, the polymeric film material may be a material having properties which allow for stretching and very little elastic return, commonly referred to as a "dead-stretch"

property. Such materials may have beneficial moldability properties as well. A non-limiting example of such a material is a thermoplastic urethane-phenoxy film. Alternatively, the barrier-side layer 320 may be a barrier-side adhesive layer formed from an adhesive material. The barrier-side layer 320 may be configured for application to a barrier of an ostomy pouch system as described further below. A distal side of the barrier-side layer 320 may form at least a portion of the barrier-facing side 314 of the ostomy accessory 310.

The ostomy accessory 310 of the present embodiments is not limited to the examples described above and shown in FIGS. 8 and 9, however. For example, in other embodiments, the ostomy accessory 310 may include a second adhesive layer, as described below with reference to FIG. 14, and the sensor layer 318 may be disposed between the first adhesive layer 316 and the second adhesive layer. In an embodiment, the second adhesive layer may be disposed between the sensor layer 318 and the barrier-side layer 320. In an embodiment, the barrier-side adhesive layer and/or the second adhesive layer may be formed from a medical-grade pressure sensitive adhesive, such as a hydrocolloid.

Figure 11:
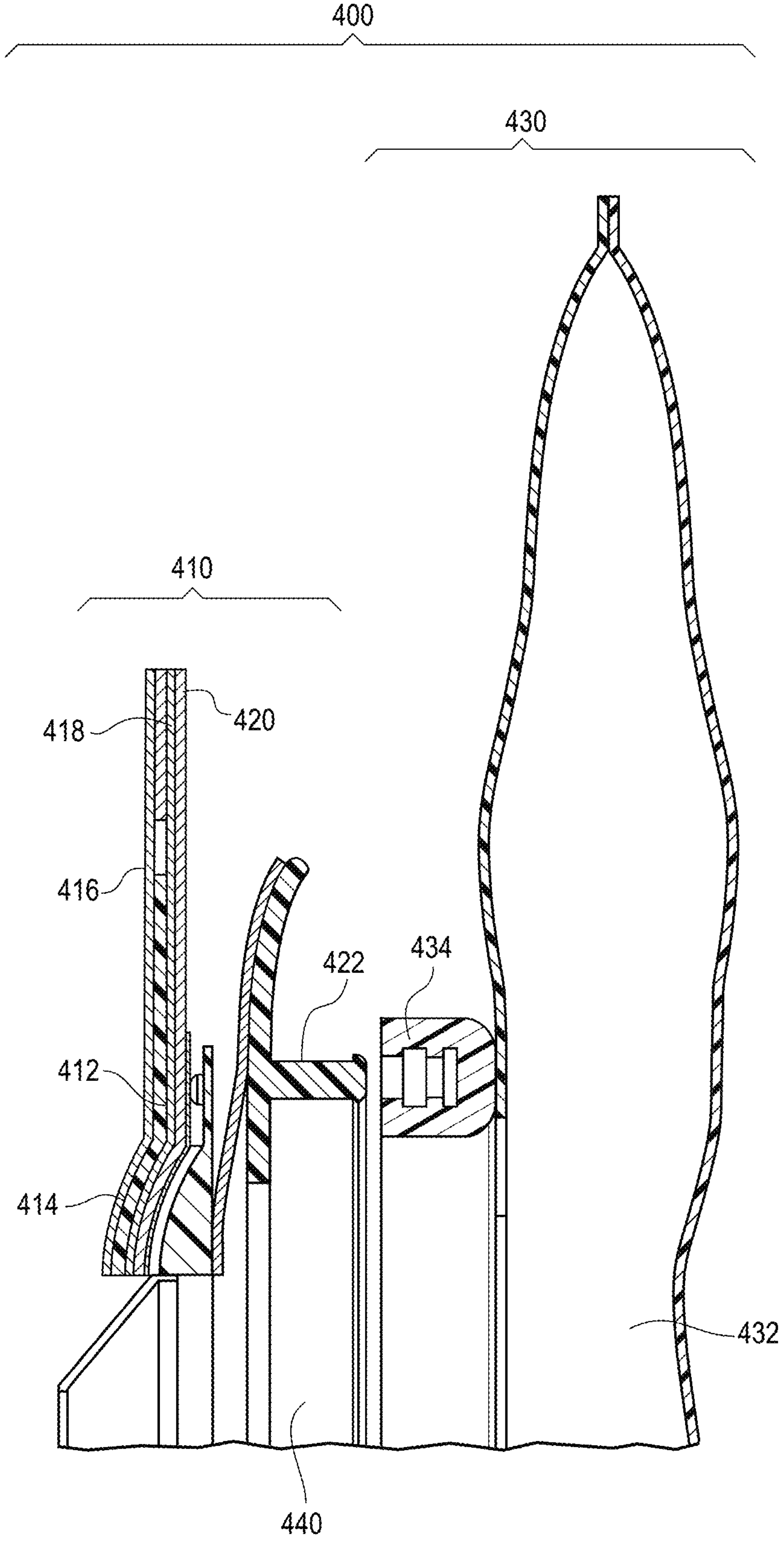
FIG. 11 is a side cross-sectional view illustrating an example of a known ostomy pouch system.

FIG. 11 is a side cross-sectional view illustrating an example of an ostomy pouch system 400 to which the ostomy accessory 310 may be applied. The ostomy pouch system 400 may be any known ostomy pouch system having a barrier and an ostomy pouch. For the purposes of example, reference is made to a specific, known ostomy pouch system 400 shown in FIG. 11. However, it is understood that the ostomy accessory 310 of the present embodiments is not limited for use with the ostomy pouch system 400 of the examples herein. Indeed, the ostomy accessory 310 of the present embodiments may be used together with any known ostomy pouch system having a barrier configured to be adhered to a patient's peristomal skin surfaces.

Referring to FIG. 11, an example of a suitable ostomy pouch system 400 with which the ostomy accessory 310 may be used includes, generally, ostomy appliance such as a barrier ring or faceplate assembly 410 having a barrier 412. The barrier 412 includes a skin attachment surface 414 conventionally configured for adhering to peristomal skin surfaces. That is, the barrier 412 is made of, or includes, an adhesive material exposed at the skin attachment surface 414 and configured to adhere to a patient's peristomal skin surfaces. The ostomy appliance, shown as faceplate assembly 410 in a non-limiting example, may optionally include a barrier release liner 416 removably disposed over the skin attachment surface 414. The faceplate assembly 410 may also optionally include an adhesive layer 418 on a distal side of the barrier 412 and a faceplate 420 at a distal side (i.e., a pouch-facing side) of the faceplate assembly 410.

The ostomy pouch system 400 may be a one-piece ostomy pouch system or a two-piece ostomy pouch system. A two-piece ostomy pouch system 400, of the type shown in FIG. 11, may further include a first coupling ring 422 at a distal side of the face plate 420.

The ostomy pouch system 400 may further include an ostomy pouch 430. The ostomy pouch 430 may have an interior volume 432 configured to receive and store stomal effluent. In a two-piece ostomy pouch system, the ostomy pouch 430 may also include a second coupling ring 434 configured for mating engagement with the first coupling ring 422.

A stoma opening 440 may extend through the faceplate assembly 410 and a body-facing side of the ostomy pouch 430. The stoma opening 440 is configured to dispose the interior volume 432 of the ostomy pouch 430 in fluid communication with the stoma, such that stomal effluent may be received in the interior volume 432 through the stoma opening 440.

Figure 12:
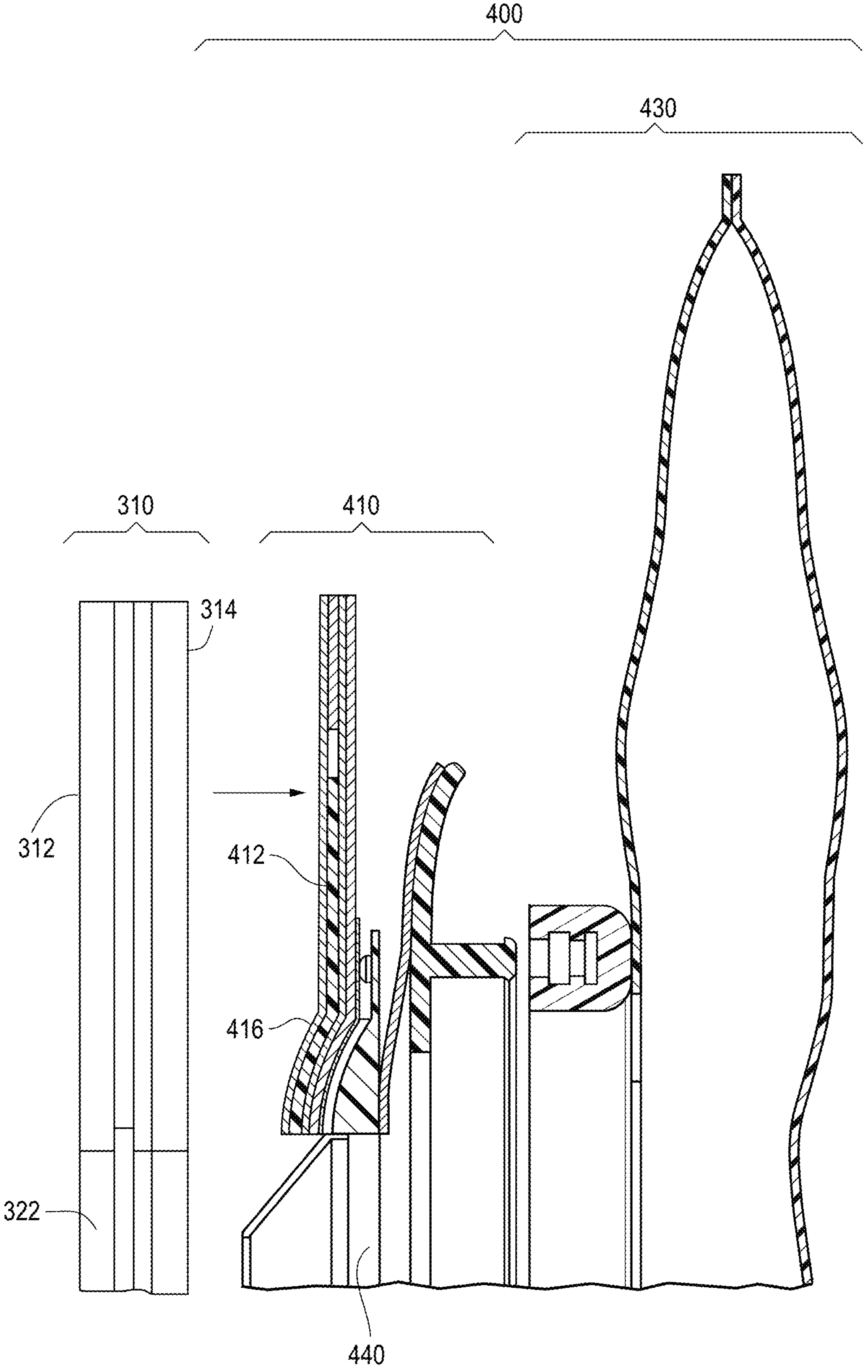
FIG. 12 is a side cross-sectional view illustrating an example of an ostomy accessory positioned for application to an ostomy pouch system according to an embodiment.

FIG. 12 is a side cross-sectional view illustrating an example of the ostomy accessory 310 positioned for application to the ostomy pouch system 400, according to an embodiment. In an embodiment, the ostomy accessory 310 may first be applied to the ostomy pouch system 400, and then applied to the patient. As shown in FIG. 12, the ostomy accessory may be positioned with the body-facing side 312 facing away from the ostomy pouch system 400 and the barrier-facing side 314 facing toward the ostomy pouch system 400.

The barrier release liner 416 of the ostomy pouch system 400 may be removed to expose the adhesive material of the barrier 412. The ostomy accessory 310 may be moved toward the barrier 412 as indicated by the arrow in FIG. 12. The barrier-facing side 314, for example, the distal side of the barrier-side layer 320, may then be adhered to the barrier 412. The stoma passage 322 of the ostomy accessory 310 and the stoma opening 440 of the ostomy pouch system 400 may be generally aligned to form a sealed passage for stomal effluent to flow from the stoma into the ostomy pouch 430.

An ostomy assembly according to embodiments herein may include the ostomy accessory 310 and the ostomy pouch system 400, including the barrier 412 and the ostomy pouch 430, wherein the barrier-facing side 314 of the ostomy accessory 310 is adhered to the adhesive material of the barrier 412.

The ostomy accessory 310 may also be configured to attach the ostomy pouch system 400 to the patient. For example, the ostomy accessory 310 may be applied to the barrier 412 of the ostomy pouch system 400 in the manner described above. The body-facing side 312 of the ostomy accessory 310, including the proximal side of the adhesive layer 316, may be adhered to the patient's peristomal skin surfaces to seal around the stoma and attach the ostomy accessory 310 and the ostomy pouch system 400 to the patient.

Figure 13:
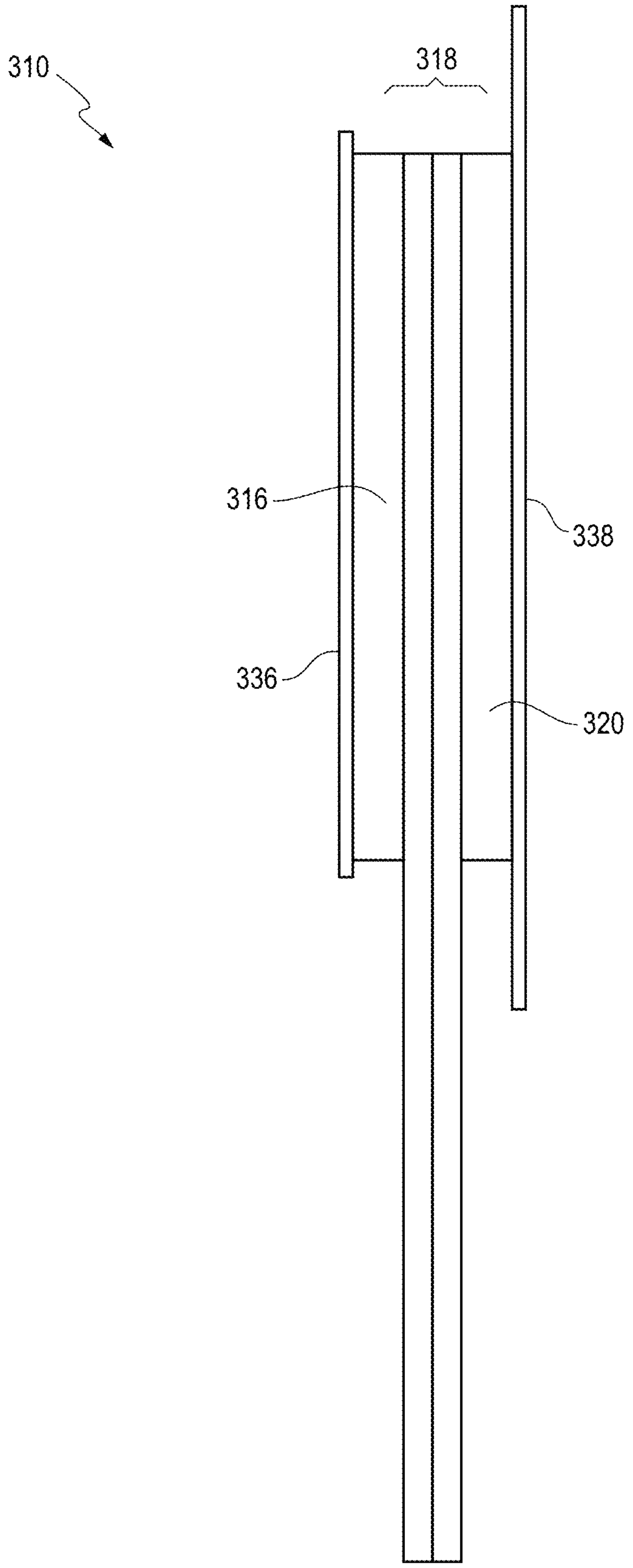
FIG. 13 is a diagram schematically illustrating another side view of the ostomy accessory according to an embodiment.

FIG. 13 is a diagram schematically illustrating another side view of the ostomy accessory 310 according to an embodiment. With reference to FIGS. 8 and 13, the ostomy accessory 310 may include a body-facing side release liner 336. The body-facing release liner 336 may extend over the body-facing side 312 of the ostomy accessory 310. In an embodiment, the body-facing release liner 336 extends over the proximal side of the adhesive layer 316. The ostomy accessory 310 may further include a barrier-facing side release liner 338. The barrier-facing side release liner 338 may extend over the barrier-facing side 314 of the ostomy accessory 310. One, or both, of the release liners 36, 38 may be included with the ostomy accessory 310, for example, for shipping and storage. In use, an end user may remove each release liner 336, 338 to expose the body-facing side 312 and the barrier-facing side 314 of the ostomy accessory 310. In some embodiments, the barrier-facing side release liner 338 may be omitted. For example, the barrier-facing side release liner 38 may be omitted when the barrier-side layer 320 is a polymeric film material. That is, in some embodiments, the barrier-facing side release liner 38 may be omitted when the barrier-side layer 320 is not an adhesive layer. Accordingly, the barrier-side layer 320, when formed as a polymeric film, may be molded to size and may be adhered directly to the ostomy pouch system 400.

Figure 14:
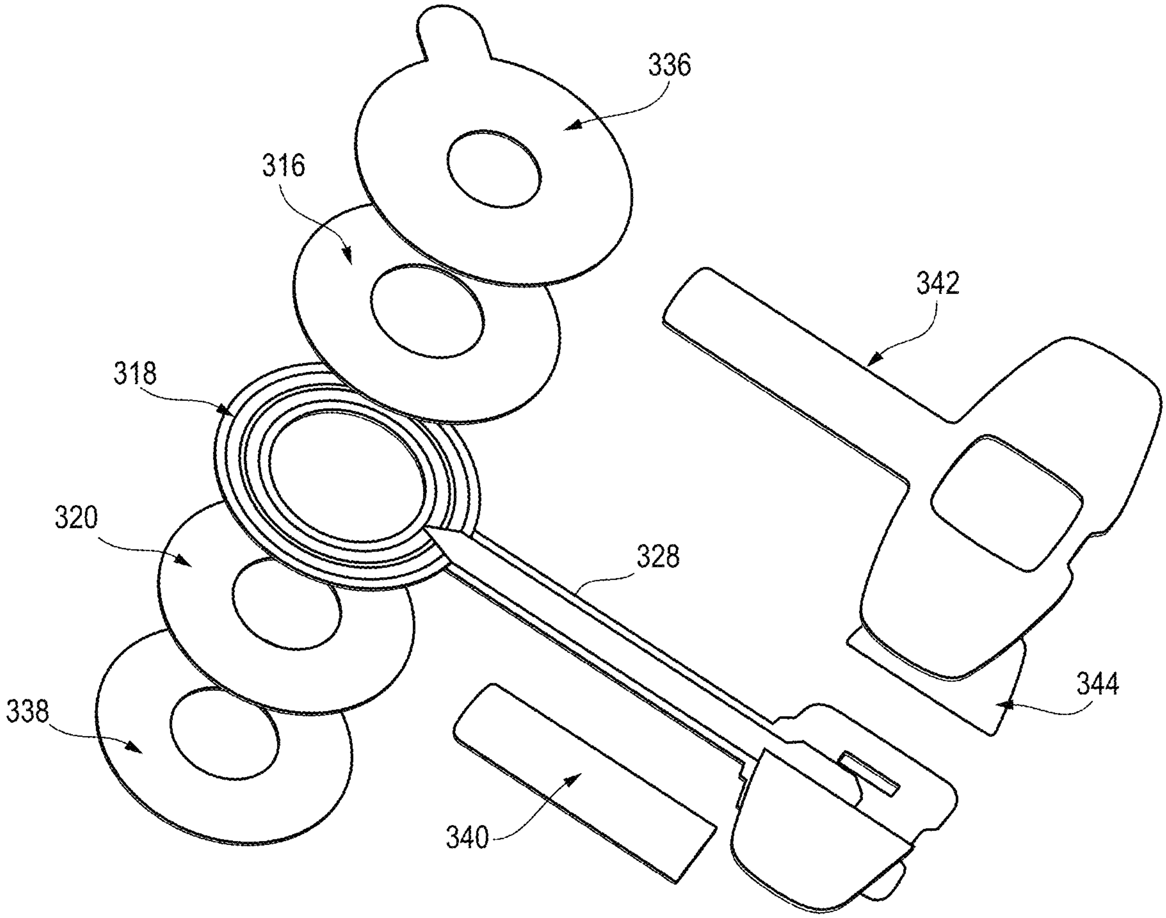
FIG. 14 is another exploded view of the ostomy accessory according to an embodiment.

FIG. 14 is an exploded view illustrating an example of the ostomy accessory 310 according to an embodiment in which the barrier-side layer 320 is a second adhesive layer. That is, in an embodiment, the ostomy accessory may include a second adhesive layer positioned for use as a barrier-side adhesive layer 320. Referring to FIG. 14, the ostomy accessory 310 may include the body-facing side release liner 336, the first adhesive layer 316, the sensor layer 318, the barrier-side layer 320 formed as a second adhesive layer, i.e., a barrier-side adhesive layer, and the barrier-facing side release liner 338.

In some embodiments, the ostomy accessory 310 may further include a barrier-side cover 340 for the sensor layer 318 and a body-side cover 342 for the sensor layer 318. In an embodiment, the barrier-side cover 340 may be disposed over a barrier-facing side of the connector section 328 and the body-side cover 342 may be disposed over a body-facing side of the connector section 328. The barrier-side cover 340 and/or the body-side cover 342 may be formed of a non-woven material in an embodiment. In an embodiment, the ostomy accessory 310 may also include a non-woven adhesive paper release liner 344.

The ostomy accessory 310 may be configured for application to the ostomy pouch system 400 by the end user, such as the patient, caretaker or other medical professional. In an embodiment, the ostomy accessory 310 may include one or more features to promote a preferred orientation and/or order of steps to apply the ostomy accessory 310 to the ostomy pouch system 400. For example, it may be preferred that the barrier-facing side 314 of the ostomy accessory 310 is oriented toward the ostomy pouch system 400 and is applied to the ostomy pouch system 400 before being applied to the patient.

For example, in an embodiment, the ostomy accessory 310 may include printed indicia or other marking to identify the body-facing side 312 and/or the barrier-facing side 314. In an embodiment, the body-facing side release liner 336 may include printed indicia such as "body-facing side" or other similar indicia to indicate the side of the ostomy accessory 310 configured to adhere to the patient's peristomal skin. Alternatively, or in addition, the body-facing side 314, and/or a distal side of the barrier-facing side release liner 338 may include printed indicia or other marking such as "barrier-facing side" or other similar indicia to indicate the side of the ostomy accessory 310 configured to be applied to the barrier 412. Other printed indicia, such as graphics, colors and the like may be suitable as well. Alternatively, or in addition, the printed indicia or other marking may be included on the sensor layer 318, for example, on the substrate 326.

Alternatively, or in addition, the body-facing side release liner 336 and the barrier-facing side release liner 338 may be asymmetrically formed. For example, the barrier-facing side release liner 338 may be larger than the body-facing side release liner 336. For instance, the barrier-facing side release liner 338 may have a larger width or diameter than the body-facing side release liner 336. In an embodiment, an outer periphery of the body-facing side release liner 336 may be entirely within an outer periphery of the barrier-facing side release liner 338. Accordingly, an end user may more easily manipulate a portion of the barrier-facing side release liner 338 for removal before removing the body-facing side release liner 336. In this manner, application of the barrier-facing side 314 of the ostomy accessory 310 to the barrier 412 may be promoted before application of the body-facing side 312 of ostomy accessory 310 to the peristomal skin surfaces of the patient.

Alternatively, or in addition, the ostomy accessory 310 may be packaged in a way which promotes the preferred orientation and/or order of steps to apply the ostomy accessory 310 to the barrier 412. For example, the ostomy accessory 310 may be packaged with the barrier-facing side 314 exposed upon opening the package. The package may be, for example, a box or a clamshell, such as a thermoformed clamshell. In an embodiment, the package may be partially comprised of a release liner. While in the package, the barrier-facing side 314 of the ostomy accessory 310 may be lined by the release liner of the package. Opening the package may remove the release liner of the package to expose the barrier-facing side 314 of the ostomy accessory 310.

In an embodiment, the ostomy accessory 310 may be packaged in a four-side film pouch. The body-facing side 312 and the barrier-facing side 314 may both be lined by the film. When opening the ostomy accessory 310, the film may be removed from the barrier-facing side 314 first, allowing the ostomy accessory 310 to be applied to the barrier 412. The film may be completely removed to expose the body-facing side 312 to the apply the ostomy accessory 310 to the patient.

As described above, the control unit 334 may be attached to the ostomy accessory 310. In an embodiment, if the control unit 334 is attached in an incorrect orientation, an electrical connection to the ostomy accessory 310 may be precluded. Accordingly, in an embodiment, the control unit 334 may be configured to check for a circuit connection to the sensor layer 316 of the ostomy accessory 310. If the control unit 334 determines that a circuit connection is not made, the control unit 334 may provide a notification to the user.

Accordingly, in the embodiments above, an ostomy accessory 310 may be provided separately from an ostomy pouch system 400, and in particular, separate from a barrier 412 or faceplate assembly 410 of an ostomy pouch system 400. In this manner, the ostomy accessory 310 of the present embodiments may be applied to a wide range of existing ostomy pouch systems and is not necessarily limited to a particular brand, model or configuration of an ostomy pouch system. Thus, an end user may selectively use the ostomy accessory 310 with existing ostomy pouch systems. As such, the end user may be presented a wide range of flexibility and options when selecting ostomy pouch systems.

The ostomy accessory 310 of the present embodiments is configured to detect leakage of stomal effluent into the seal formed between the adhesive layer 316 and the peristomal skin surfaces. The ostomy accessory 310 is further configured to provide an alert or notification when such a leak is detected. In an embodiment, a location of the leak may be determined as well. In this manner, the patient may be notified of a stomal effluent leak and thus, may replace the ostomy accessory 310 and optionally, the ostomy pouch system 400. Accordingly, prolonged exposure of peristomal skin to the leaking stomal effluent may be avoided. In addition, by detecting and notifying of stomal fluid leakage, the ostomy accessory 310 may be replaced before the stomal effluent leak propagates to an outer periphery of the ostomy accessory 310 or barrier 412.

Further, the ostomy accessory 310 of the present embodiments may include features to promote correct orientation and/or preferred application process of the ostomy accessory 310 to the barrier 412.

It is understood that various features or components described with respect to any of the embodiments above may be combined with, used together with, or replace features or components described with respect to any of the other embodiments.

All patents referred to herein, are hereby incorporated herein in their entirety, by reference, whether or not specifically indicated as such within the text of this disclosure.

In the present disclosure, the words "a" or "an" are to be taken to include both the singular and the plural. Conversely, any reference to plural items shall, where appropriate, include the singular. In additions, various features described with respect to any of the embodiments above may be used together, implemented in, or replace features in any of the other embodiments described above.

From the foregoing it will be observed that numerous modifications and variations can be effectuated without departing from the true spirit and scope of the novel concepts of the present invention. It is to be understood that no limitation with respect to the specific embodiments illustrated is intended or should be inferred. The disclosure is intended to cover by the appended claims all such modifications as fall within the scope of the claims.

What is claimed is:

1. An ostomy device comprising:

a proximal side configured for attachment to a user;

a distal side opposite to the proximal side; and a leakage detection sensor comprising electrically conductive circuitry supported on a support layer, wherein the leakage detection sensor is configured to detect ostomy effluent by detecting a change in resistance in the electrically conductive circuitry, wherein the ostomy device is an ostomy accessory configured to be attached to an ostomy appliance including an adhesive barrier, wherein the distal side is attached to a proximal side of the adhesive barrier of the ostomy appliance.

2. The ostomy device of claim 1, wherein the support layer is a skin barrier and the proximal side is a proximal side of the skin barrier.

3. The ostomy device of claim 2, wherein the leakage detection sensor is configured to detect ostomy effluent by detecting a change in a resistance in the skin barrier.

4. The ostomy device of claim 3, wherein the leakage detection sensor includes at least one resistance sensor, wherein the at least one resistance sensor is configured to detect a change in resistance.

5. The ostomy device of claim 3, wherein the leakage detection sensor is configured to determine a location of an ostomy effluent leak and includes a plurality of resistance sensors.

6. The ostomy device of claim 3, wherein the leakage detection sensor includes a ring-shaped body formed from a flexible printed circuit board and a plurality of resistance sensors arranged on the ring-shaped body.

7. The ostomy device of claim 6, wherein the plurality of resistance sensors are arranged in at least two rows, wherein the resistance sensors arranged in a first row are closer to a center of the leakage detection sensor than the resistance sensors arranged in a second row.

8. The ostomy device of claim 7, wherein the plurality of resistance sensors are arranged in at least two different quadrants of the ring-shaped body.

9. The ostomy device of claim 5, wherein the leakage detection sensor is configured to determine a location of an ostomy effluent leak by associating a signal indicating a change in resistance to a location of the resistance sensor generating the signal.

10. The ostomy device of claim 5, wherein the leakage detection sensor is configured to track a progress of an ostomy effluent leak by associating a first signal indicating a change in resistance to a location of the resistance sensor generating the first signal and associating a second signal indicating a change in resistance to a location of the resistance sensor generating the second signal.

11. The ostomy device of claim 1, wherein the support layer is a substrate and the leakage detection sensor is disposed between a skin barrier and a backing layer, the leakage detection sensor includes at least one resistances sensor, and the proximal side is a proximal side of the skin barrier.

12. The ostomy device of claim 11, further comprising at least one wicking component configured to facilitate transport of the ostomy effluent toward the leakage detection sensor.

13. The ostomy device of claim 12, wherein the at least one wicking component is configured to reduce a signal noise by filtering out at least some solid components in the ostomy effluent.

14. The ostomy device of claim 13, wherein the at least one wicking component is configured to saturate at a threshold liquid volume, wherein the at least one resistance sensor is configured to generate a consistent signal at or above the threshold liquid volume, wherein the leakage detection sensor is configured to generate an alarm when the consistent signal is received.

15. The ostomy device of claim 12, wherein the skin barrier includes at least one cut-out configured to contain the at least one wicking component.

16. The ostomy device of claim 1, wherein the leakage detection sensor includes a plurality of resistance sensors formed of eight pairs of conductive traces arranged in two rows and in four quadrants of the ring-shaped body, wherein the ostomy device comprises eight wicking components, each of the wicking components configured and arranged to cover an adjacent conductive trace pair, wherein the skin barrier includes eight cut-outs configured to contain the eight wicking components, wherein the ostomy device further comprises a backing layer, and wherein the leakage detection sensor is arranged between the skin barrier and the backing layer.

17. The ostomy device of claim 2, wherein the leakage detection sensor is a leak detection system configured to identify an ostomy effluent leakage event by detecting a change in resistance of a user's skin.

18. The ostomy device of claim 17, wherein the leak detection system includes at least one pair of electrodes arranged on a body-side surface of the skin barrier, wherein each of the at least one pair of electrodes is configured to measure resistance of a portion of user's skin adjacent the electrode pair, wherein the body-side surface is at the proximal side.

19. The ostomy device of claim 18, wherein the at least one pair of electrodes are formed from a plurality of resistance sensors.

20. The ostomy device of claim 18, wherein the leak detection system is configured to identify an ostomy effluent leakage event by detecting a change in resistance of a user's skin resulting from a presence of ostomy effluent at an intersection between the skin barrier and the user's skin.

21. The ostomy device of claim 18, wherein the leak detection system is configured to identify a skin inflammation event by detecting a change in resistance of a user's skin.

* * * * *